United States Patent [19]
Soyama et al.

[11] Patent Number: 5,672,339
[45] Date of Patent: Sep. 30, 1997

[54] COMPOSITION FOR ROUGE FOR LIP

[75] Inventors: Yoshikazu Soyama; Takashi Minami; Hirotaka Takada; Junko Hirayama; Akio Nasu, all of Yokohama, Japan

[73] Assignee: Shiseido Co., Ltd., Tokyo, Japan

[21] Appl. No.: 693,097

[22] PCT Filed: Sep. 29, 1995

[86] PCT No.: PCT/JP95/01995

§ 371 Date: Aug. 9, 1996

§ 102(e) Date: Aug. 9, 1996

[87] PCT Pub. No.: WO96/18375

PCT Pub. Date: Jun. 20, 1996

[30] Foreign Application Priority Data

| Dec. 16, 1994 | [JP] | Japan | 6-334199 |
| May 31, 1995 | [JP] | Japan | 7-158642 |
| May 31, 1995 | [JP] | Japan | 7-158643 |
| Jun. 29, 1995 | [JP] | Japan | 7-186155 |
| Sep. 21, 1995 | [JP] | Japan | 7-269314 |
| Sep. 21, 1995 | [JP] | Japan | 7-269315 |

[51] Int. Cl.$^6$ .................................................. A61K 7/021
[52] U.S. Cl. .................. 424/63; 424/61; 424/64; 424/81; 514/772; 514/844; 514/845
[58] Field of Search ................... 424/63, 64, 61, 424/81, DIG. 5; 514/844, 845, 772

[56] References Cited

FOREIGN PATENT DOCUMENTS

| 62-12710 | 1/1987 | Japan . |
| 63-183516 | 7/1988 | Japan . |
| 2287312 | 11/1990 | Japan . |
| 5-186313 | 7/1993 | Japan . |
| 5186313 | 7/1993 | Japan . |
| 6009339 | 1/1994 | Japan . |
| 6-9339 | 1/1996 | Japan . |

*Primary Examiner*—Terressa Mosley
*Attorney, Agent, or Firm*—Ronald R. Snider

[57] ABSTRACT

A composition for rouge for lip of the present invention is a composition for rouge for lip containing a volatile oil content, a water-repellent polymer soluble to the volatile oil content, powder, and a nonvolatile oil content having a compatibility with the volatile oil content, wherein the powder contained in 1 g of the composition has a total surface arm of 1 to 25 m$^2$.

According to the composition for rouge for lip of the present invention, a composition for rouge for lip in which the secondary adhesion is improved and feel of use is excellent can be obtained.

31 Claims, No Drawings

COMPOSITION FOR ROUGE FOR LIP

[TECHNICAL FIELD]

The present invention relates to a composition for rouge for lip and, in particular, to an improvement in the secondary adhesion thereof.

[BACKGROUND ART]

The rouge for lip is one of very popular cosmetics. Due to its characteristic of being applied to lip, it should be bland and harmless to the lip while yielding no unpleasant taste or smell, for example.

Recently, there has been a strong demand for improving so-called secondary adhesion in which the rouge applied to the lip is transferred thereafter to portions of cups or the like which come into contact with the lip.

Accordingly, in recent years, there has been reported a "cosmetic composition having an improved anti-transfer characteristic" disclosed in Japanese Unexamined Patent Publication Hei No. 6-199630. This cosmetic composition is characterized in that it contains a volatile solvent, a silicone resin, wax, powder, and an oil content. The secondary adhesion is supposed to be improved when such a cosmetic composition is used.

However, the above-mentioned cosmetic composition is still problematic about the spreadability at the time of its application and the smooth feel of use. Also, the problem of its secondary adhesion has not completely been eliminated and is yet to be improved.

Also, the rouge for lip should be smoothly attached to the lip, and this smooth feel of use should be maintained. Since the improvement of the above-mentioned secondary adhesion is contrary to the maintenance of the smooth feel of use, it has been difficult to develop a composition for rouge for lip having both of these characteristics.

[DISCLOSURE OF INVENTION]

In view of the problems of the prior art mentioned above, the object of the present invention is to provide a composition for rouge for lip in which the secondary adhesion is further improved together with smooth feel of use.

As the result of diligent studies conducted by the inventors in order to attain the above-mentioned object, it has been found that, a composition for rouge for lip in which both smooth feel of use and secondary adhesion are improved can be obtained when the relationship between a water-repellent polymer and a powder, the relationship between the polymer and its solvent, and the relationship between the polymer and a wax are taken into account, thereby accomplishing the present invention.

Namely, the first aspect of the composition for rouge for lip in accordance with the present invention contains a volatile oil content, a water-repellent polymer soluble to the volatile oil content, a powder, and a nonvolatile oil content having a compatibility with the volatile oil content, wherein the powder contained in 1 g of the composition has a total surface area of 1 to 25 m$^2$.

Preferably, the above-mentioned composition contains 10 to 60% by weight of the volatile oil content, 5 to 35% by weight of the water-repellent polymer, 1 to 25% by weight of the powder, and 5 to 40% by weight of the nonvolatile oil content.

Also, preferably, the above-mentioned composition contains 10 to 50% by weight of the volatile oil content, 10 to 35% by weight of the water-repellent polymer, 1 to 25% by weight of the powder, and 10 to 40% by weight of the nonvolatile oil content.

The second aspect of the composition for rouge for lip in accordance with the present invention is characterized in that, in the above-mentioned composition for rouge for lip, the powder is capable of being coated with the water-repellent polymer in a state where the volatile oil content does not exist.

In this composition, at least a part of the powder is preferably silica.

Also, preferably, this composition contains 20 to 60% by weight of the volatile oil content, 5 to 20% by weight of the water-repellent polymer, 1 to 10% by weight of silica, and 5 to 30% by weight of the nonvolatile oil content.

The third aspect of the composition for rouge for lip in accordance with the present invention is characterized in that at least a part of the powder is titanated mica.

Also, preferably, this composition contains 10 to 50% by weight of the volatile oil content, 10 to 35% by weight of the water-repellent polymer, 1 to 10% by weight of titanated mica, and 10 to 40% by weight of the nonvolatile oil content.

Also, this composition preferably has a amount ratio of titanated mica/water-repellent polymer of 1/30 to 1/3.

Also, this composition preferably has a amount ratio of titanated mica/water-repellent polymer of 1/10 to 1/4.

The fourth aspect of the composition for rouge for lip in accordance with the present invention is characterized in that, in the above-mentioned composition for rouge for lip, at least a large-size particle and an ultrafine particle exist as the powder, wherein the ultrafine particle has a particle size of 0.01 to 0.1 μm while the ratio of the particle size of the ultrafine particle to the particle size of the large-size particle is 1:20 to 1:500.

Here, preferably, this composition contains 10 to 50% by weight of the volatile oil content, 10 to 35% by weight of the water-repellent polymer, 2 to 20% by weight of the powder, and 10 to 40% by weight of the nonvolatile oil content.

Also, in this composition, the amount ratio of the ultrafine particle to the large-size particle is preferably 1:19 to 10:1.

Also, in this composition, the ultrafine particle is preferably ultrafine silica.

The fifth aspect of the composition for rouge for lip in accordance with the present invention contains a volatile oil content, a water-repellent polymer soluble to the volatile oil content, a powder, and a nonvolatile oil content having a compatibility with the volatile oil content, wherein the water-repellent oil content and the nonvolatile oil content are selected from those which yield a turbidity of 9.0 to 25.5 when they are mixed alone.

Here, preferably, this composition contains 10 to 50% by weight of the volatile oil content, 10 to 35% by weight of the water-repellent polymer, and 10 to 40% by weight of the nonvolatile oil content.

In this composition, as the nonvolatile oil content, an oil content which plasticize water-repellent polymer and an oil content which does not plasticize water repellent polymer are preferably used to adjust the turbidity.

Also, in this composition, at least a part of the powder is preferably silica.

Also, preferably, this composition contains 0.1 to 10% by weight of silica.

The sixth aspect of the composition for rouge for lip in accordance with the present invention contains a volatile oil content, a water-repellent polymer soluble to the volatile oil content, wax dispersible in the volatile oil content, and a nonvolatile oil content having a compatibility with the volatile oil content, wherein the compounding ratio of the water-repellent polymer to the wax is 10/3 to 5/7.

Here, preferably, this composition contains 10 to 50% by weight of the volatile oil content, 10 to 35% by weight of the water-repellent polymer, 5 to 25% by weight of the wax, and 10 to 40% by weight of the nonvolatile oil content.

Also, preferably, this composition further contains powder.

Also, preferably, this composition contains 1 to 20% by weight of the powder.

Also, in this composition, at least a part of the powder is silica.

Also, preferably, this composition contains 1 to 10% by weight of silica.

The seventh aspect of the composition for rouge for lip in accordance with the present invention is characterized in that water is further compounded in any of the above-mentioned compositions.

Here, this composition preferably contains 0.05 to 5% by weight of water.

Also, in this composition, water compounded therein is preferably natural water.

Also, preferably, in any of the above-mentioned compositions for rouge for lip, the volatile oil content is a silicone oil, while the water-repellent polymer is a silicone resin.

Also, preferably, in any of the above-mentioned compositions for rouge for lip, the weight ratio of the water-repellent polymer to the nonvolatile oil content is 1/2 to 2/1.

Here, in this description, "total surface area" refers to the sum of the surface area of the powder contained in 1 g of the composition. Also, "turbidity" refers to L value measured by the method explained in the following. Also, "having a plasticizing capacity" means that the capacity of the non-volatile oil content for dissolving the water-repellent polymer is 30% by weight or higher, whereas "having no plasticizing capacity" means that the capacity of the non-volatile oil content for dissolving the water-repellent polymer is 5% by weight or lower.

[Method of Measuring Turbidity]

1. A mixed sample is prepared as a volatile oil content, a water-repellent polymer, and a nonvolatile oil content are mixed together with their respective ratios identical to those in the composition.

2. Into a middle-sized black dish of 2.8×1.9×0.3 cm³, 0.2 g of the above-mentioned mixed sample is poured and then left for 6 hours at 90° C. so as to completely volatilize the volatile oil content.

3. The turbidity of thus obtained sample measured as L value by means of a colorimeter is defined as the turbidity.

In the following, the configuration of the present invention will be explained in detail. Prior to explanation of effects obtained by combination of individual constituents, each constituent will be explained.

Volatile Oil Content

Examples of the volatile oil content preferably used in the present invention include chain polysiloxanes such as decamethyltetrasiloxane, hexamethyldisiloxane, and dodecamethylpentasiloxane; cyclic polysiloxanes such as octamethylcyclotetrasiloxane and decamethylcyclopentasiloxane; and light liquid isoparaffins such as Shellsol (Shell Chemical) and Isopar (Esso Chemical).

Water-Repellent Polymer

Examples of the water-repellent polymer preferably used in the present invention include silicone resins, silicone rubbers, fluorine-denatured silicone resins, and alkyl-denatured silicone resins. In particular, silicone resins are preferable.

Specifically, there is a silicone resin expressed by a mean formula (1):

$$RnSiO_{(4-n)/2} \tag{1}$$

wherein R is a hydrocarbon group having 1 to 6 carbon atoms or phenyl group and n is a value from 1.0 to 1.8. Preferably, this silicone resin comprises an appropriate combination selected from the group consisting of $R_3SiO_{1/2}$ unit, $R_2SiO$ unit, $RSiO_{2/3}$ unit, and $SiO_2$ unit and has a mean molecular weight of about 1,500 to 20,000.

Nonvolatile Oil Content

For the nonvolatile oil content preferably used in the present invention, any of nonvolatile oil contents having a high safety to the skin can be used. Examples thereof include liquid paraffins, squalane, castor oil, olive oil, jojoba oil, glyceryl diisostearate, trimethylolpropane tri-2-ethyl isostearate, isopropyl myristate, cetyl-2-ethyl hexanoate, glyceryl triisostearate, 2-heptylundecyl palmitate, methylpolysiloxane, polybutene, glycerine triisostearate, diisostearyl malate, and lanolin. One or at least two kinds are arbitrarily selected therefrom.

Powder

As the powder preferably used in the present invention, any of the powders normally used in cosmetics can be used. Examples thereof include inorganic powders such as talc, kaolin, sericite, muscovite, phlogopite, synthetic mica, lepidolite, biotite, lithia mica, titanated mica, vermiculite, magnesium carbonate, calcium carbonate, aluminum silicate, barium silicate, calcium silicate, magnesium silicate, strontium silicate, metal tungstate, magnesium, silica, zeolite, bentonite, barium sulfate, calcined calcium sulfate (calcined gypsum), calcium phosphate, fluorine apatite, hydroxy apatite, ceramic powder, boron nitride, titanium dioxide, and zinc oxide; organic powders such as polyamide resin powder, nylon powder, polyethylene powder, polypropylene powder, polyester powder, polymethyl methacrylate powder, polystyrene powder, styrene/acrylic acid copolymer powder, silicone resin powder, benzoguanamine resin powder, polyethylene tetrafluoride powder, and cellulose powder; and pigments.

Wax

In the present invention, a wax can be compounded in order to improve the secondary adhesion together with the water-repellent polymer or as a shape-retaining agent for forming a lipstick. Examples of the wax used in the present invention include ceresin wax, carnauba wax, polyethylene wax, paraffin wax, candelilla wax, microcrystalline wax, behenic acid, behenyl alcohol, Japan tallow, beeswax, and cetanol.

Other Ingredients

In the composition for rouge for lip in accordance with the present invention, various ingredients normally compounded in cosmetics such as rouge for lip, for example, antioxidant, UV-absorber, UV-screening agent, antiseptic, humectant, and dye, may be compounded.

Correlation With Total Surface Area Of Powder In Composition

The first aspect of the compound for rouge for lip in accordance with the present invention is characterized in that the powder in the composition has a total surface area of 1 to 25 m². Here, as the powder, one or at least two kinds of powder may be used. When at least two kinds of powder are used, their specific surface areas may be the same or different from each other.

In accordance with the present invention, due to the above-mentioned configuration, the water-repellent polymer, powder, nonvolatile oil content, and the like are dissolved or dispersed in the volatile oil content as the product form before application, while it spreads well when being applied, whereby smooth feel of use can be obtained.

After being applied to lip, the volatile oil content is volatilized, whereas the water-repellent polymer, the powder, and the nonvolatile oil content remain on the lip. When the water-repellent polymer and the nonvolatile oil content coexist, stickiness is remarkable. It is supposed that, when the total surface area of the powder in the composition is adjusted as in the case of the present invention, the powder attracts the water-repellent polymer and the nonvolatile oil content so as to suppress the stickiness caused by them, thereby improving the secondary adhesion.

Here, in this composition, the suitable amount of the volatile oil content is 10 to 60% by weight and, preferably, 10 to 50% by weight. When it is less than 10%, the amount of the other ingredients become relatively large, whereby the spreadability at the time of application may deteriorate. When it exceeds 60% by weight, on the other hand, the amount of the other ingredients become relatively small, whereby the secondary adhesion may not be improved sufficiently. Since the composition may become liquid when this amount exceeds 50% by weight, the volatile oil content is more preferably 10 to 50% by weight.

The suitable amount of the water-repellent polymer is 5 to 35% by weight, preferably, 10 to 35% by weight, and, more preferably, 15 to 30% by weight. When the amount of the water-repellent polymer is less than 5% by weight, the secondary adhesion may not be improved at all. When it is compounded 10% by weight or more, the improvement of the secondary adhesion becomes more favorable. When the amount of the water-repellent polymer exceeds 35% by weight, on the other hand, the spreadability may deteriorate while stickiness may occur. Accordingly, it is more preferably 30% by weight or less.

The suitable amount of the powder is preferably 1 to 25% by weight even when the preferable range of its total surface area is satisfied. The stickiness may not be suppressed sufficiently when the powder is less than 1% by weight, whereas the feel of use may deteriorate when it exceeds 25% by weight.

The suitable amount of the nonvolatile oil content is 5 to 40% by weight, preferably, 10 to 40% by weight, and, more preferably, 15 to 30% by weight. When the nonvolatile oil content is less than 5% by weight, the feel after application and dry may deteriorate. When it exceeds 40% by weight, on the other hand, the problem of the secondary adhesion may occur.

Here, in the present invention, as a shape-retaining agent for constituting a lipstick, 5 to 20% by weight of a wax may be compounded.

Compounding Of Silica

The second aspect of the composition for rouge for lip is characterized in that the powder can be coated with the water-repellent polymer in a state where the volatile oil content does not exist. As such a powder, silica is preferable in particular. In this composition, both feel of use and secondary adhesion are favorably improved when the amount of silica is 1 to 10% by weight and, more preferably, 1 to 8% by weight.

In accordance with the present invention, due to the above-mentioned configuration, the water-repellent polymer, silica, nonvolatile oil content, and the like are dissolved or dispersed in the volatile oil content as the product form before application, while it spreads well when being applied, whereby smooth feel of use can be obtained.

After being applied to lip, the volatile oil content is volatilized, whereas the water-repellent polymer, silica, and the nonvolatile oil content remain on the lip. In general, stickiness is remarkable when the water-repellent polymer is used alone. It is supposed that, in the present invention, as silica is compounded, this powder suppresses the stickiness of the water-repellent polymer.

The suitable amount of the volatile oil content in this composition is 10 to 60% by weight and, preferably, 20 to 60% by weight. When it is less than 10%, the other ingredients become relatively large, whereby the spreadability at the time of application may deteriorate. When it exceeds 60% by weight, on the other hand, the amount of the other ingredients become relatively small, whereby the secondary adhesion may not be improved sufficiently. In particular, in view of the feel of use, it is preferably 20 to 60% by weight.

The suitable amount of the water-repellent polymer is preferably 5 to 20% by weight and, more preferably, 7 to 15% by weight. When the amount of the water-repellent polymer is less than 5% by weight, the secondary adhesion may not be improved at all. When the amount of the water-repellent polymer exceeds 20% by weight, on the other hand, stickiness may occur. Accordingly, it is more preferably 15% by weight or less.

The preferable total amount of the powder is 1 to 25% by weight and, in particular, 1 to 20% by weight. The stickiness may not be suppressed sufficiently when the powder is less than 1% by weight, whereas the feel of use may deteriorate when it exceeds 25% by weight. In particular, both feel of use and secondary adhesion are favorably improved when silica is used 1 to 10% by weight and, more preferably, 1 to 8% by weight.

The suitable amount of the nonvolatile oil content is preferably 5 to 30% by weight and, more preferably, 7 to 15% by weight. When the nonvolatile oil content is less than 5% by weight, the feel of the composition after application and dry may deteriorate. When it exceeds 30% by weight, on the other hand, stickiness may occur.

Here, in the present invention, as a shape-retaining agent for constituting a lipstick, 5 to 20% by weight of a wax may be compounded.

Compounding Of Titanated Mica

The third aspect of the composition for rouge for lip in accordance with the present invention is characterized in that at least a part of the powder is titanated mica. In particular, both feel of use and secondary adhesion are favorably improved when titanated mica is used 1 to 10% by weight and, more preferably, 1 to 8% by weight.

Here, "titanated mica" refers to materials in which mica is coated with titanium oxide or titanium compound. Preferably, those in which mica:titanium is 80:20 to 50:50 are used. Also, those containing iron oxide, ultramarine, carmine, and the like, in addition to mica and titanium, may be used.

In accordance with the present invention, due to the above-mentioned configuration, the water-repellent polymer, titanated mica, nonvolatile oil content, and the like are dissolved or dispersed in the volatile oil content as the product form before application, while it spreads well when being applied, whereby smooth feel of use can be obtained.

After being applied to lip, the volatile oil content is volatilized, whereas the water-repellent polymer, titanated mica, and the nonvolatile oil content remain on the lip. It is supposed that, when the water-repellent polymer is compounded, as titanated mica is compounded together with the nonvolatile oil content, titanated mica suppresses the stickiness of the water-repellent polymer and improves the secondary adhesion while yielding luster of the lip.

Here, the suitable amount of the volatile oil content in this composition is 10 to 60% by weight and, preferably, 10 to 50% by weight. When it is less than 10%, the other ingredients become relatively large, whereby there may be lack of the spreadability at the time of application. When it exceeds 60% by weight, on the other hand, the amount of the other ingredients become relatively small, whereby the secondary adhesion may not be improved sufficiently. Since the composition may become liquid when this amount exceeds 50% by weight, the volatile oil content is more preferably 10 to 50% by weight in particular.

The suitable amount of the water-repellent polymer is 5 to 35% by weight, preferably, 10 to 35% by weight, and, more preferably, 15 to 30% by weight. When the amount of the water-repellent polymer is less than 5% by weight, the secondary adhesion may not be improved at all. When it is compounded 10% by weight or more, the secondary adhesion is improved more favorably. When the amount of the water-repellent polymer exceeds 35% by weight, on the other hand, stickiness may occur. Accordingly, it is more preferably 30% by weight or less.

The suitable amount of the powder is preferably 1 to 25% by weight and, more preferably, 1 to 20% by weight. The stickiness may not be suppressed sufficiently when the powder is less than 1% by weight, whereas the feel of use may deteriorate when it exceeds 25% by weight.

Further, in the present invention, the amount ratio of titanated mica to the water-repellent polymer is preferably 1/30 to 1/3 and, more preferably, 1/10 to 1/4. When it is 1/3 or more, the spreadability may deteriorate. When it is 1/30 or less, on the other hand, stickiness may occur and the secondary adhesion may not be improved sufficiently. When it is 1/10 to 1/4, a composition for rouge for lip excellent in all the usabilities and secondary adhesion can be obtained.

The suitable amount of the nonvolatile oil content is 5 to 40% by weight, preferably, 10 to 40% by weight, and, more preferably, 15 to 30% by weight. When the nonvolatile oil content is less than 5% by weight, the feel after application and dry may deteriorate. When it exceeds 40% by weight, on the other hand, stickiness may occur.

Here, in the present invention, as a shape-retaining agent for constituting a lipstick, 5 to 20% by weight of a wax may be compounded.

Correlation With Combination Of Ultrafine Particle And Large-Size Particle

The fourth aspect of the composition for rouge for lip in accordance with the present invention is characterized in that at least a large-size particle and an ultrafine particle exist as the powder, while the ultrafine particle has a particle size of 0.01 to 0.1 μm and the ratio of the particle size of the ultrafine particle to the particle size of the large-size particle is 1:20 to 1:500. Here, examples of the ultrafine particle include ultrafine silica, ultrafine titanium dioxide, ultrafine barium sulfate, and ultrafine zinc white. Among them, ultrafine silica is preferably used in particular.

In accordance with the present invention, due to the above-mentioned configuration, the water-repellent polymer, powder, nonvolatile oil content, and the like are dissolved or dispersed in the volatile oil content as the product form before application, while it spreads well when being applied, whereby smooth feel of use can be obtained.

After being applied to lip, the volatile oil content is volatilized, whereas the water-repellent polymer, the powder, and the nonvolatile oil content remain on the lip. In general, stickiness is remarkable when the water-repellent polymer is used alone. It is supposed that, in the present invention, as the powder comprising the ultrafine particle such as ultrafine silica and the large-size particle is compounded, this powder suppresses the stickiness of the water-repellent polymer. Also, it is supposed that, as the ultrafine particle and the large-size particle are compounded, luster is rendered to the lip when the composition is in use.

Here, the suitable amount of the volatile oil content in this composition is 10 to 60% by weight and, preferably, 10 to 50% by weight. When it is less than 10%, the amount of the other ingredients become relatively large, whereby the spreadability at the time of application may deteriorate. When it exceeds 60% by weight, on the other hand, the amount of the other ingredients become relatively small, whereby the secondary adhesion may not be improved sufficiently. Since the composition may become liquid when this amount exceeds 50% by weight, the volatile oil content is preferably 10 to 50% by weight in particular.

The suitable amount of the water-repellent polymer is 5 to 35% by weight, preferably, 10 to 35% by weight, and, more preferably, 15 to 30% by weight. When the amount of the water-repellent polymer is less than 5% by weight, the secondary adhesion may not be improved at all. When it is compounded 10% by weight or more, the secondary adhesion is improved more favorably. When the amount of the water-repellent polymer exceeds 35% by weight, on the other hand, stickiness may occur. Accordingly, it is more preferably 30% by weight or less.

The preferable amount of the powder is 1 to 25% by weight and, in particular, 2 to 20% by weight. The stickiness may not be suppressed sufficiently when the powder is less than 1% by weight, whereas the feel of use may deteriorate when it exceeds 25% by weight. In the present invention, both feel of use and secondary adhesion are favorably improved when the ultrafine particle is used 1 to 10% by weight and, more preferably, 1 to 8% by weight.

In this composition, the amount ratio of the ultrafine particle to the large-size particle is preferably 1:19 to 10:1. When the amount of the large-size particle is too large with respect to the ultrafine particle, stickiness may occur at the time of use. When the amount of the large-size particle is too small, on the other hand, the spreadability at the time of application may deteriorate and no luster may be obtained after application.

The suitable amount of the nonvolatile oil content is 5 to 40% by weight, preferably, 10 to 40% by weight, and, more preferably, 15 to 30% by weight. When the nonvolatile oil content is less than 5% by weight, the feel after application and dry may deteriorate. When it exceeds 40% by weight, on the other hand, stickiness may occur.

Here, in the present invention, as a shape-retaining agent for constituting a lipstick, 5 to 20% by weight of a wax may be compounded.

Correlation With Turbidity Of Water-Repellent Polymer And Nonvolatile Oil Content The fifth aspect of the composition for rouge for lip in accordance with the present invention is characterized in that the water-repellent oil content and the nonvolatile oil content are adjusted so as to yield a turbidity of 9.0 to 25.5 when they are mixed alone. When the turbidity is 8.9 or less, the secondary adhesion may not be improved sufficiently, whereby stickiness may occur. When it is 25.6 or more, on the other hand, luster may be insufficient, while stickiness and spreadability may become unfavorable, thereby yielding the secondary adhesion.

In accordance with the present invention, due to the above-mentioned configuration, the water-repellent polymer, powder, nonvolatile oil content, and the like are dissolved or dispersed in the volatile oil content as the product form before application, while it spreads well when being applied, whereby smooth feel of use can be obtained.

After being applied to lip, the volatile oil content is volatilized, whereas the water-repellent polymer, the powder, and the nonvolatile oil content remain on the lip. In general, stickiness is remarkable when the water-repellent polymer is used alone. It is supposed that, in the present invention, as the turbidity of the water-repellent polymer and the nonvolatile oil content is maintained within a predetermined range so as to adjust the solubility of the water-repellent polymer, the spreadability is prevented from deteriorating, the stickiness is suppressed, luster is rendered, and the secondary adhesion is improved.

As the nonvolatile oil content used in the present invention, an oil content which plasticize water-repellent polymer and an oil content which does not plasticize water-repellent polymer may be appropriately combined together so as to adjust the turbidity of the water-repellent polymer and nonvolatile oil content.

Here, the suitable amount of the volatile oil content in this composition is 10 to 60% by weight and, preferably, 10 to 50% by weight. When it is less than 10%, the other ingredients become relatively large, whereby the spreadability at the time of application may deteriorate. When it exceeds 60% by weight, on the other hand, the amount of the other ingredients become relatively small, whereby the secondary adhesion may not be improved sufficiently. Since the composition may become liquid when this amount exceeds 50% by weight, the volatile oil content is preferably 10 to 50% by weight in particular.

The suitable amount of the water-repellent polymer is 5 to 35% by weight, preferably, 10 to 35% by weight, and, more preferably, 15 to 30% by weight. When the amount of the water-repellent polymer is less than 5% by weight, the secondary adhesion may not be improved at all. When it is compounded 10% by weight or more, the secondary adhesion is improved more favorably. When the amount of the water-repellent polymer exceeds 35% by weight, on the other hand, stickiness may occur. Accordingly, it is more preferably 30% by weight or less.

The preferable amount of the powder is 0.1 to 25% by weight and, in particular, 0.1 to 20% by weight. The stickiness may not be suppressed sufficiently when the powder is less than 0.1% by weight, whereas the feel of use may deteriorate when it exceeds 25% by weight. In particular, both feel of use and secondary adhesion are favorably improved when silica is used 0.1 to 10% by weight and, more preferably, 1 to 8% by weight.

The suitable amount of the nonvolatile oil content is 5 to 40% by weight, preferably, 10 to 40% by weight, and, more preferably, 15 to 30% by weight. When the nonvolatile oil content is less than 5% by weight, the feel after application and dry may deteriorate. When it exceeds 40% by weight, on the other hand, stickiness may occur.

Here, in the present invention, as a shape-retaining agent for constituting a lipstick, 5 to 20% by weight of a wax may be compounded.

Correlation With Water-Repellent Polymer And Wax

The sixth aspect of the composition for rouge for lip in accordance with the present invention is characterized in that, in the composition for rouge for lip in which a water-repellent polymer and wax are compounded, the amount ratio of the water-repellent polymer to the wax is 10/3 to 5/7. When it is 10/3 or more, stickiness may occur while the secondary adhesion may not be improved sufficiently. When it is 5/7 or less, powdery feel may occur while the secondary adhesion may not be improved sufficiently.

In accordance with the present invention, due to the above-mentioned configuration, the water-repellent polymer, wax, nonvolatile oil content, and the like are dissolved or dispersed in the volatile oil content as the product form before application, while it spreads well when being applied, whereby smooth feel of use can be obtained.

After being applied to lip, the volatile oil content is volatilized, whereas the water-repellent polymer, the wax, the nonvolatile oil content, and the like remain on the lip. It is supposed that, though the coating by the wax alone is easily peeled off, when the wax and a water-repellent polymer such as silicone resin coexist so as to form crosslink, the secondary adhesion can be improved.

Further, the water-repellent polymer alone yields stickiness in general, whereas the wax alone yields powdery feel in general. In the present invention, it is supposed that, as the water-repellent polymer and the wax are combined together, the stickiness of the water-repellent polymer and the powdery feel of the wax are suppressed.

Here, the suitable amount of the volatile oil content in this composition is 10 to 60% by weight and, preferably, 10 to 50% by weight. When it is less than 10%, the amount of the other ingredients become relatively large, whereby the spreadability at the time of application may deteriorate. When it exceeds 60% by weight, on the other hand, the amount of the other ingredients become relatively small, whereby the secondary adhesion may not be improved sufficiently. Since the composition may become liquid when this amount exceeds 50% by weight, the volatile oil content is preferably within the range of 10 to 50% by weight in particular.

The suitable amount of the water-repellent polymer is 5 to 35% by weight, preferably, 10 to 35% by weight, and, more preferably, 15 to 30% by weight. When the amount of the water-repellent polymer is less than 5% by weight, the secondary adhesion may not be improved at all. When it is compounded 10% by weight or more, the secondary adhesion is improved more favorably. When the amount of the water-repellent polymer exceeds 35% by weight, on the other hand, stickiness may occur. Accordingly, it is more preferably 30% by weight or less.

The suitable amount of the powder is preferably 1 to 25% by weight and, more preferably, 1 to 20% by weight. The stickiness may not be suppressed sufficiently when the powder is less than 1% by weight, whereas the feel of use may deteriorate when it exceeds 25% by weight. In particular, both feel of use and secondary adhesion can be favorably improved when silica is used 1 to 10% by weight and, more preferably, 1 to 8% by weight.

The suitable amount of the nonvolatile oil content is 5 to 40% by weight, preferably, 10 to 40% by weight, and, more preferably, 15 to 30% by weight. When the nonvolatile oil content is less than 5% by weight, the feel after application and dry may deteriorate. When it exceeds 40% by weight, on the other hand, stickiness may occur.

The suitable amount of the wax is 5 to 25% by weight. When it is less than 5% by weight, sufficient water repellency may not be guaranteed. When it exceeds 25% by weight, on the other hand, powdery feel may occur on the surface to which it is applied. The wax used here also functions as a shape-retaining agent at the time of making the product.

Correlation With Compounding Of Water

The seventh aspect of the composition for rouge for lip in accordance with the present invention is characterized in that water is compounded in any of the above-mentioned compositions as an additional ingredient for improving "wetness" and "luster." When natural water is used therefor, greater effects are attained.

Here, "natural water" refers to spring water from the underground and surface of the earth generally known as natural water, natural mineral water, and mineral water (Guidelines for Quality Indication of Mineral Water, published Mar. 20, 1990, Japan Ministry of Agriculture, Forestry and Fisheries; collectively referred to as "natural water" hereinafter) in the field of drinking water and the like.

While any of drinkable underground water or surface water may be used as natural water in the present invention, suitable examples thereof, in particular, include that derived from the foothills of Mount Fuji (various places around Yamanashi and Shizuoka Prefectures), Mount Rokko in Hyogo Prefecture, Mount Tanigawadake in Gunma Prefecture, the foothills of the Japan South Alps, the foothills of the Japan North Alps, Hokusetsu Mountain System in Osaka Prefecture, Oomine Mountain System in Iwate Prefecture, Yamazaki in Kyoto Prefecture, Mount Kurama in Kyoto Prefecture, Kirishima Mountain System in Kagoshima Prefecture, Yaku Island in Kagoshima Prefecture, and Azuma Mountain System in Fukushima and Yamagata Prefectures.

Examples thereof also include water derived from Nasu Mountain System in Tochigi Prefecture, Nikko Mountain Range, Akagi Mountain System in Gunma Prefecture, Musashi Hill in Saitama Prefecture, Chichibu Mountain System, Sanbu County in Chiba Prefecture, Mejirodai in the Metropolis of Tokyo, Tanzawa Mountain System in Kanagawa Prefecture, the west foothills of Mount Fuji in Yamanashi Prefecture, Asagiri Heights, the Misaka Pass in Koufu, the spa of Shimobe in the foothills of Mount Fuji, the Sasago Pass, Nishi-Katsura Town, Mount Kai-Komagatake in the Japan South Alps, Numazu City in Shizuoka Prefecture, Ryugaiwa Cave, Matsumoto City in Nagano Prefecture, Azumino, Kamikochi, Karuizawa, Mount Kiso-Ontake, the foothills of Mount Komagatake in the Japan Central Alps, Echigo Mountain System in Niigata Prefecture, Hakusan in Ishikawa Prefecture, Otowa Mountain System in Shiga Prefecture, Kitayama in Kyoto Prefecture, Mount Kurama, the spa of Daimonji, the foothills of Mount Kongo in Osaka Prefecture, Mount Nose-Yoshino, Tanba, the foothills of Mount Gomadan in Wakayama Prefecture, Naka-Hiruzen in Okayama Prefecture, and Kamo Plateau in Hiroshima Prefecture.

In the present invention, one or at least two kinds of natural water derived from these water source areas are preferably used. Though not restricted in particular, the amount thereof in the composition for rouge for lip is 0.05 to 5% by weight and, preferably, 0.1 to 2% by weight. When it is less than 0.05% by weight, sufficient wetness and luster may not be obtained. When it exceeds 5% by weight, on the other hand, the secondary adhesion may occur.

[BEST MODE FOR CARRYING OUT THE INVENTION]

In the following, the present invention will be explained in further detail with reference to preferred embodiments of the present invention. However, the present invention should not be restricted to the following examples. Here, the amount is indicated by % by weight unless otherwise indicated in particular. Also, the evaluation of usability was effected according to the following method.

[Method of Evaluating Usability]

For each example, an panel for cosmetics consisting of 20 members is used for its usability test. Here, the evaluation was based on the following standards:

⊚: 16 to 20 members judged favorably.

○: 11 to 15 members judged favorably.

△: 8 to 10 members judged favorably.

x: 0 to 5 members judged favorably.

(1) Correlation With Total Surface Area Of Powder In Composition

First, the inventors prepared lipsticks with the following compositions and investigated their feel of use, secondary adhesion, and the like. Here, in each of the test examples hereinafter, a small amount of a surface active agent is used. The compositions and results are shown in Table-1.

TABLE 1

| | Test Example | | | | | | |
|---|---|---|---|---|---|---|---|
| | 1-1 | 1-2 | 1-3 | 1-4 | 1-5 | 1-6 | 1-7 |
| Volatile Oil Content | | | | | | | |
| Octamethylcyclotetra-siloxane | 34.8 | 33.8 | 31.8 | 29.8 | 26.8 | 24.8 | 19.8 |
| Nonvolatile Oil Content | | | | | | | |
| Liquid paraffin | 20 | 20 | 20 | 20 | 20 | 20 | 20 |
| Castor oil | 0.2 | 0.2 | 0.2 | 0.2 | 0.2 | 0.2 | 0.2 |
| Polymer | | | | | | | |
| Silicone resin A | 25 | 25 | 25 | 25 | 25 | 25 | 25 |
| Powder | | | | | | | |
| Silica (Specific surface area 200 $m^2/g$) | 0 | 1 | 3 | 5 | 8 | 10 | 15 |
| Pigment (Specific surface area 2 $m^2/g$) | 5 | 5 | 5 | 5 | 5 | 5 | 5 |
| Wax | | | | | | | |
| Ceresin wax | 15 | 15 | 15 | 15 | 15 | 15 | 15 |
| Total surface area ($m^2$) | 0.1 | 2.1 | 6.1 | 10.1 | 16.1 | 20.1 | 30.1 |
| Spreadability | ⊚ | ⊚ | ⊚ | ⊚ | ⊚ | ○ | x |
| Luster | ○ | ○ | ○ | ○ | ○ | ○ | x |
| Secondary adhesion | x | ○ | ⊚ | ⊚ | ⊚ | ⊚ | ⊚ |
| Stickiness | x | ○ | ⊚ | ⊚ | ⊚ | ⊚ | ⊚ |

Here, as water-repellent silicone resin A, a silicone resin (referred to as "silicone resin A" hereinafter) which has a molecular weight of about 3,000 and is expressed by a mean formula of $(CH_3)_{1.33}SiO_{1.34}$ with $(CH_3)_3SiO_{1/2}:SiO_2$ unit= 0.8:1 is used.

As can be seen from the above results, when pigment alone is compounded as the powder, the total surface area becomes 0.1 $m^2$, whereby no improvement is observed at all in the secondary adhesion and stickiness at the time of use. Also, when the total surface area of the compounded powder is 0.1 $m^2$, no improvement in the secondary adhesion is observed, while no sufficient results are obtained with respect to stickiness. Further, when the total surface area is 30.1 $m^2$, though the secondary adhesion is improved, spreadability is unfavorable and luster cannot be attained sufficiently.

Further studies were conducted by using silica with different specific surface areas. The compositions and results are shown in Table-2.

TABLE 2

| | Test Example | | | | | | |
|---|---|---|---|---|---|---|---|
| | 1-8 | 1-9 | 1-10 | 1-11 | 1-12 | 1-13 | 1-14 |
| Volatile Oil Content | | | | | | | |
| Octamethylcyclotetra-siloxane | 44.8 | 39.8 | 34.8 | 29.8 | 24.8 | 19.8 | 14.8 |
| Nonvolatile Oil Content | | | | | | | |
| Liquid paraffin | 20 | 20 | 20 | 20 | 20 | 20 | 20 |
| Castor oil | 0.2 | 0.2 | 0.2 | 0.2 | 0.2 | 0.2 | 0.2 |
| Polymer | | | | | | | |
| Silicone resin A | 20 | 20 | 20 | 20 | 20 | 20 | 20 |
| Powder | | | | | | | |
| Silica (Specific surface area 10 m²/g) | 0 | 5 | 10 | 15 | 20 | 25 | 30 |
| Pigment (Specific surface area 2 m²/g) | 5 | 5 | 5 | 5 | 5 | 5 | 5 |
| Wax | | | | | | | |
| Ceresin wax | 15 | 15 | 15 | 15 | 15 | 15 | 15 |
| Total surface area (m²) | 0.1 | 0.6 | 1.1 | 1.6 | 2.1 | 2.6 | 3.1 |
| Spreadability | ⊚ | ⊚ | ⊚ | ⊚ | ⊚ | ○ | ○ |
| Luster | ○ | ○ | ○ | ○ | ○ | ○ | ○ |
| Secondary adhesion | X | X | ○ | ○ | ○ | ⊚ | ⊚ |
| Stickiness | X | X | ○ | ○ | ○ | ⊚ | ⊚ |

As can be seen from the above results, when the total surface area is 1.0 m² or less, the improvement in the secondary adhesion and stickiness becomes insufficient. Also, when the surface area was 1.0 m² or higher, all the evaluations were favorable while the secondary adhesion was sufficiently improved.

Accordingly, in view of the results shown in Tables-1 and 2, the total surface area should be 1 to 25 m².

Further, the inventors conducted studies by compounding different kinds of powders. The compositions and results are shown in Table-3.

TABLE 3

| | Test Example | | | | | |
|---|---|---|---|---|---|---|
| | 1-15 | 1-16 | 1-17 | 1-18 | 1-19 | 1-20 |
| Volatile Oil Content | | | | | | |
| Octamethylcyclotetrasiloxane | 24.8 | 14.8 | 29.8 | 24.8 | 29.8 | 24.8 |
| Nonvolatile Oil Content | | | | | | |
| Liquid paraffin | 20 | 20 | 20 | 20 | 20 | 20 |
| Castor oil | 0.2 | 0.2 | 0.2 | 0.2 | 0.2 | 0.2 |
| Polymer | | | | | | |
| Silicone resin A | 25 | 25 | 25 | 25 | 25 | 25 |
| Powder | | | | | | |
| Zinc white (Specific surface area 13 m²/g) | 10 | 20 | — | — | — | — |
| Barium sulfate (Specific surface area 19 m²/g) | — | — | 5 | 10 | — | — |
| Titanium oxide (Specific surface area 41 m²/g) | — | — | — | — | 5 | 10 |
| Pigment (Specific surface area 2 m²/g) | 5 | 5 | 5 | 5 | 5 | 5 |
| Wax | | | | | | |
| Ceresin wax | 15 | 15 | 15 | 15 | 15 | 15 |
| Total surface area | 1.4 | 2.7 | 1.05 | 2.0 | 2.15 | 4.2 |
| Spreadability | ⊚ | ○ | ⊚ | ⊚ | ○ | ○ |
| Luster | ○ | ○ | ○ | ○ | ○ | ○ |

TABLE 3-continued

| | Test Example | | | | | |
|---|---|---|---|---|---|---|
| | 1-15 | 1-16 | 1-17 | 1-18 | 1-19 | 1-20 |
| Secondary adhesion | ○ | ⊚ | ⊚ | ⊚ | ⊚ | ⊚ |
| Stickiness | ○ | ⊚ | ⊚ | ⊚ | ⊚ | ⊚ |

As can be seen from the above results, also in the case where powders having different specific surface areas are compounded, a composition for rouge for lip with improved secondary adhesion, favorable spreadability, and improved luster and stickiness can be obtained when the total surface area satisfies the above-mentioned condition.

Accordingly, the total surface area of the powder in 1 g of the composition should be 1 to 25 m².

Next, the inventors studied the effective amount of each ingredient.

Amount Of Water-Repellent Polymer

First, the inventors studied the amount of the water-repellent polymer. Here, the total surface area is 10.1 m². The compositions and results are shown in Table-4.

TABLE 4

| | Test Example | | | | | | | |
|---|---|---|---|---|---|---|---|---|
| | 1-21 | 1-22 | 1-23 | 1-24 | 1-25 | 1-26 | 1-27 | 1-28 |
| Volatile Oil Content | | | | | | | | |
| Octamethyl-cyclotetra-siloxane | 50 | 45 | 40 | 35 | 30 | 25 | 20 | 15 |
| Nonvolatile Oil Content | | | | | | | | |
| Liquid paraffin | 20 | 20 | 20 | 20 | 20 | 20 | 20 | 20 |
| Polymer | | | | | | | | |
| Silicone resin A | 5 | 10 | 15 | 20 | 25 | 30 | 35 | 40 |
| Powder | | | | | | | | |
| Silica (Specific surface area 200 m²/g) | 5 | 5 | 5 | 5 | 5 | 5 | 5 | 5 |
| Pigment (Specific surface area 2 m²/g) | 5 | 5 | 5 | 5 | 5 | 5 | 5 | 5 |
| Wax | | | | | | | | |
| Ceresin wax | 15 | 15 | 15 | 15 | 15 | 15 | 15 | 15 |
| Spreadability | ○ | ○ | ○ | ○ | ○ | ○ | ○ | Δ |
| Luster | ○ | ○ | ○ | ○ | ○ | ○ | ○ | ○ |
| Secondary adhesion | Δ | ○ | ⊚ | ⊚ | ⊚ | ⊚ | ⊚ | ⊚ |
| Stickiness | ⊚ | ⊚ | ⊚ | ⊚ | ⊚ | ⊚ | ○ | Δ |

As can be seen from the above results, even when the total surface area satisfies its condition, in order to improve the secondary adhesion, the water-repellent polymer is preferably 10% by weight or more. When the water-repellent polymer exceeds 35% by weight, however, stickiness may occur or spreadability may deteriorate. Accordingly, it more preferably does not exceed 30% by weight.

Amount Of Powder

Next, the inventors studied the amount of the powder. The compositions and results are shown in Table-5.

TABLE 5

| | Test Example | | | | | | |
|---|---|---|---|---|---|---|---|
| | 1-29 | 1-30 | 1-31 | 1-32 | 1-33 | 1-34 | 1-35 |
| Volatile Oil Content | | | | | | | |
| Octamethylcyclotetra-siloxane | 39.5 | 39 | 35 | 30 | 25 | 20 | 15 |
| Nonvolatile Oil Content | | | | | | | |
| Liquid paraffin | 20 | 20 | 20 | 20 | 20 | 20 | 20 |
| Polymer | | | | | | | |
| Silicone resin A | 20 | 20 | 20 | 20 | 20 | 20 | 20 |
| Powder | | | | | | | |
| Silica (Specific surface area 200 m²/g) | 5 | 5 | 5 | 5 | 5 | 5 | 5 |
| Pigment (Specific surface area 2 m²/g) | 0.5 | 1 | 5 | 10 | 15 | 20 | 25 |
| Wax | | | | | | | |
| Ceresin wax | 15 | 15 | 15 | 15 | 15 | 15 | 15 |
| Total amount of powder | 5.5 | 6 | 10 | 15 | 20 | 25 | 30 |
| Total surface area | 10.01 | 10.02 | 10.1 | 10.2 | 10.3 | 10.4 | 10.5 |
| Spreadability | ○ | ○ | ○ | ○ | ○ | ○ | ○ |
| Luster | ○ | ○ | ○ | ○ | ○ | ○ | ○ |
| Secondary adhesion | ○ | ⊚ | ⊚ | ⊚ | ⊚ | ⊚ | ⊚ |
| Stickiness | ⊚ | ⊚ | ⊚ | ⊚ | ⊚ | ○ | Δ |
| Powdery feel | ⊚ | ⊚ | ⊚ | ⊚ | ⊚ | ○ | Δ |

As can be seen from the above results, even in the case where the total surface area of the powder satisfies its condition, when the total amount is 25% by weight or more, spreadability deteriorates while stickiness occurs. Also, the ratio of the powder with respect to the composition is so high that the powdery feel remains.

Further, the inventors conducted studies in the region where the amount of the powder is small. The results are shown in Table-6.

TABLE 6

| | Test Example | | | | | | |
|---|---|---|---|---|---|---|---|
| | 1-36 | 1-37 | 1-38 | 1-39 | 1-40 | 1-41 | 1-42 |
| Volatile Oil Content | | | | | | | |
| Octamethylcyclotetrasiloxane | 44.7 | 44.2 | 43.7 | 41.7 | 39.7 | 36.7 | 34.7 |
| Nonvolatile Oil Content | | | | | | | |
| Liquid paraffin | 20 | 20 | 20 | 20 | 20 | 20 | 20 |
| Polymer | | | | | | | |
| Silicone resin A | 20 | 20 | 20 | 20 | 20 | 20 | 20 |
| Powder | | | | | | | |
| Silica (Specific surface area 200 m²/g) | 0 | 0.5 | 1 | 3 | 5 | 8 | 10 |
| Pigment (Specific surface area 2 m²/g) | 0.3 | 0.3 | 0.3 | 0.3 | 0.3 | 0.3 | 0.3 |
| Wax | | | | | | | |
| Ceresin wax | 15 | 15 | 15 | 15 | 15 | 15 | 15 |
| Total amount of Powder | 0.3 | 0.8 | 1.3 | 3.3 | 5.3 | 8.3 | 10.3 |
| Total surface area | 0.006 | 1.006 | 2.006 | 6.006 | 10.006 | 16.006 | 20.006 |
| Spreadability | ⊚ | ⊚ | ⊚ | ⊚ | ⊚ | ⊚ | ⊚ |
| Luster | ○ | ○ | ○ | ○ | ○ | ○ | ○ |
| Secondary adhesion | Δ | ⊚ | ⊚ | ⊚ | ⊚ | ⊚ | ⊚ |
| Stickiness | Δ | Δ | ⊚ | ⊚ | ⊚ | ⊚ | ⊚ |

As can be seen from the above results, even in the case where the total surface area of the powder satisfies its condition, when the total amount of the powder is less than 1% by weight, slight stickiness may occur. Accordingly, in view of Table-5 and Table-6, the total amount of the powder is preferably 1 to 25% by weight.

Amount Of Nonvolatile Oil Content

Next, the inventors studied the amount of the nonvolatile oil content. Here, the total surface area is 10.1 m². The compositions and results are shown in Table-7.

TABLE 7

| | Test Example | | | | | | | | |
|---|---|---|---|---|---|---|---|---|---|
| | 1-43 | 1-44 | 1-45 | 1-46 | 1-47 | 1-48 | 1-49 | 1-50 | 1-51 |
| Volatile Oil Content | | | | | | | | | |
| Octamethylcyclotetrasiloxane | 50 | 45 | 40 | 35 | 30 | 25 | 20 | 15 | 10 |
| Nonvolatile Oil Content | | | | | | | | | |
| Liquid paraffin | 5 | 10 | 15 | 20 | 25 | 30 | 35 | 40 | 45 |
| Polymer | | | | | | | | | |
| Silicone resin A | 20 | 20 | 20 | 20 | 20 | 20 | 20 | 20 | 20 |
| Powder | | | | | | | | | |
| Silica (Specific surface area 200 m²/g) | 5 | 5 | 5 | 5 | 5 | 5 | 5 | 5 | 5 |
| Pigment (Specific surface area 2 m²/g) | 5 | 5 | 5 | 5 | 5 | 5 | 5 | 5 | 5 |
| Wax | | | | | | | | | |
| Ceresin wax | 15 | 15 | 15 | 15 | 15 | 15 | 15 | 15 | 15 |
| Spreadability | Δ | ○ | ○ | ○ | ○ | ○ | ○ | ○ | ○ |
| Luster | ○ | ○ | ⊙ | ⊙ | ⊙ | ⊙ | ⊙ | ⊙ | ⊙ |
| Secondary adhesion | ○ | ○ | ⊙ | ⊙ | ⊙ | ⊙ | ○ | ○ | Δ |
| Stickiness | Δ | ○ | ⊙ | ⊙ | ⊙ | ⊙ | ○ | ○ | Δ |

As can be seen from the above results, when the nonvolatile oil content is 5% by weight, spreadability is unfavorable while stickiness occurs. When the nonvolatile oil content becomes 45% by weight, on the other hand, the stickiness and the secondary adhesion are not improved sufficiently. Accordingly, the amount of the nonvolatile oil content is preferably 10 to 40% by weight.

Ratio of Oil Content to Polymer

In the process of the foregoing studies, the inventors have found that the ratio of the nonvolatile oil content to the water-repellent polymer greatly influences the feel of use and the secondary adhesion.

Namely, it seems that, when the nonvolatile oil content is relatively very small, the influence of the water-repellent polymer is exhibited strongly, whereby stickiness may occur while spreadability may deteriorate; whereas, when the water-repellent polymer is relatively very small, the action of the water-repellent polymer is inhibited by the nonvolatile oil content, whereby the secondary adhesion or the like deteriorates. The compositions and results are shown in Table-8.

TABLE 8

| | Test Example | | | | | | | |
|---|---|---|---|---|---|---|---|---|
| | 1-52 | 1-53 | 1-54 | 1-55 | 1-56 | 1-57 | 1-58 | 1-59 |
| Nonvolatile Oil Content | | | | | | | | |
| Liquid paraffin | 5 | 10 | 14.9 | 19.8 | 24.7 | 29.5 | 34.3 | 39.0 |
| Castor oil | — | — | 0.1 | 0.2 | 0.3 | 0.5 | 0.7 | 1.0 |
| Volatile Oil Content | | | | | | | | |
| Octamethyl-cyclotetra-siloxane Polymer | 30 | 30 | 30 | 30 | 30 | 30 | 30 | 30 |
| Silicone resin A | 40 | 35 | 30 | 25 | 20 | 15 | 10 | 5 |

TABLE 8-continued

| | Test Example | | | | | | | |
|---|---|---|---|---|---|---|---|---|
| | 1-52 | 1-53 | 1-54 | 1-55 | 1-56 | 1-57 | 1-58 | 1-59 |
| Powder | | | | | | | | |
| Silica (Specific surface area 200 m²/g) | 5 | 5 | 5 | 5 | 5 | 5 | 5 | 5 |
| Pigment (Specific surface area 200 m²/g) | 5 | 5 | 5 | 5 | 5 | 5 | 5 | 5 |
| Wax | | | | | | | | |
| Ceresin wax | 15 | 15 | 15 | 15 | 15 | 15 | 15 | 15 |
| Resin/Nonvolatile Oil | 8/1 | 7/2 | 2/1 | 5/4 | 4/5 | 1/2 | 2/7 | 1/8 |
| Spreadability | X | Δ | ○ | ○ | ○ | ○ | ○ | ○ |
| Luster | Δ | Δ | ○ | ○ | ○ | ○ | ○ | ○ |
| Secondary adhesion | X | Δ | ⊙ | ⊙ | ⊙ | ○ | Δ | X |
| Stickiness | X | Δ | ○ | ⊙ | ⊙ | ⊙ | ⊙ | ⊙ |

As can be seen from the above results, when the ratio of the resin to nonvolatile oil content exceeds 2/1, spreadability and luster slightly deteriorate, while no considerable improvement in the second adhesion, stickiness, and the like is observed. Also, when the ratio of the resin to the nonvolatile oil content is less than 1/2, the characteristic of the resin cannot be exhibited sufficiently such that the effect for improving the secondary adhesion may be insufficient.

Accordingly, the ratio of the resin to the nonvolatile oil content is preferably at least 1/2 but not more than 2/1.

(2) Correlation With Compounding Of Silica

The inventors prepared lipsticks with the following compositions and investigated their feel of use, secondary adhesion, and the like. Here, in each of the test examples hereinafter, a small amount of a surface active agent is used. The compositions and results are shown in Table-9.

TABLE 9

| | Test Example | | | | |
|---|---|---|---|---|---|
| | 2-1 | 2-2 | 2-3 | 2-4 | 2-5 |
| Nonvolatile Oil Content | | | | | |
| Castor oil | 20 | 20 | 20 | 20 | 20 |
| Glyceryl diisostearate | 10 | 10 | 10 | 10 | 10 |
| Volatile Oil Content | | | | | |
| Octamethylcyclotetrasiloxane Polymer | 50 | 35 | 30 | 35 | 30 |
| Silicone resin A (Repellent) | — | — | — | 15 | 15 |
| Resin B (No-repellent) | — | 15 | 15 | — | — |
| Powder | | | | | |
| Silica | — | — | 5 | — | 5 |
| Pigment | 5 | 5 | 5 | 5 | 5 |
| Wax | | | | | |
| Ceresin wax | 15 | 15 | 15 | 15 | 15 |
| Spreadability | ○ | ○ | ○ | ○ | ○ |
| Luster | ○ | ○ | ○ | ○ | ○ |
| Secondary adhesion | X | Δ | Δ | ○ | ○ |
| Stickiness | ○ | X | Δ | X | ○ |

Here, resin B is polyvinyl methyl ether.

As can be seen from the above results, in the case where no polymer is compounded, while there is no problem with respect to spreadability, luster, stickiness, and the like, the secondary adhesion is not improved sufficiently (Test Example 2-1). On the other hand, though the secondary adhesion is likely to be improved when the polymer is compounded, not only the improvement of the secondary adhesion is insufficient but also remarkable stickiness occurs when a polymer having no water-repellency is used (Test Example 2-2). Accordingly, in order to improve the stickiness of this polymer, the inventors studied the use of powder. Then, when silica was compounded together with a polymer having no water-repellency, stickiness was somewhat improved (Test Example 2-3). When a water-repellent polymer is used as the polymer, on the other hand, though the secondary adhesion is greatly improved, stickiness remains (Test Example 2-4). It has been found, however, that, when silica is used together with the water-repellent polymer, a lipsticks in which both secondary adhesion and stickiness are favorable can be obtained (Test Example 2-5).

Next, the inventors studied the effective amount of each ingredient.

Amount Of Water-Repellent Polymer

First, the inventors studied the amount of the water-repellent polymer. The compositions and results are shown in Table-10.

TABLE 10

| | Test Example | | | | | | | | |
|---|---|---|---|---|---|---|---|---|---|
| | 2-6 | 2-7 | 2-8 | 2-9 | 2-10 | 2-11 | 2-12 | 2-13 | 2-14 |
| Nonvolatile Oil Content | | | | | | | | | |
| Castor oil | 10 | 10 | 10 | 10 | 10 | 10 | 10 | 10 | 10 |
| Volatile Oil Content | | | | | | | | | |
| Octamethylcyclo-tetrasiloxane Polymer | 60 | 58 | 56 | 53 | 50 | 48 | 46 | 43 | 38 |
| Silicone resin (Repellent) Powder | 3 | 5 | 7 | 10 | 13 | 15 | 17 | 20 | 25 |
| Silica | 7 | 7 | 7 | 7 | 7 | 7 | 7 | 7 | 7 |
| Pigment | 5 | 5 | 5 | 5 | 5 | 5 | 5 | 5 | 5 |
| Wax | | | | | | | | | |
| Ceresin wax | 15 | 15 | 15 | 15 | 15 | 15 | 15 | 15 | 15 |
| Spreadability | ○ | ○ | ○ | ○ | ○ | ○ | ○ | ○ | ○ |
| Luster | ○ | ○ | ○ | ○ | ○ | ○ | ○ | ○ | ○ |
| Secondary adhesion | Δ | ○ | ◎ | ◎ | ◎ | ◎ | ◎ | ◎ | ◎ |
| Stickiness | ◎ | ◎ | ◎ | ◎ | ◎ | ◎ | ○ | ○ | Δ |

As can be seen from the above results, in order to improve the secondary adhesion, the water-repellent polymer is preferably 5% by weight or more and, in particular, 7% by weight or more. When the water-repellent polymer exceeds 20% by weight, however, stickiness may occur. Accordingly, it more preferably does not exceed 15% by weight.

Amount Of Powder

Next, the inventors studied the amount of the powder. The compositions and results are shown in Table-11.

TABLE 11

| | Test Example | | | | | | | | |
|---|---|---|---|---|---|---|---|---|---|
| | 2-15 | 2-16 | 2-17 | 2-18 | 2-19 | 2-20 | 2-21 | 2-22 | 2-23 |
| Nonvolatile Oil Content | | | | | | | | | |
| Castor oil | 20 | 20 | 20 | 20 | 20 | 20 | 20 | 20 | 20 |
| Volatile Oil Content | | | | | | | | | |
| Octamethylcyclotetrasiloxane Polymer | 49.5 | 49 | 48 | 45 | 42 | 40 | 35 | 32 | 30 |
| Silicone resin (Repellent) Powder | 10 | 10 | 10 | 10 | 10 | 10 | 10 | 10 | 10 |
| Silica | 0.5 | 1.0 | 2.0 | 5.0 | 8.0 | 10.0 | 15.0 | 18.0 | 20.0 |
| Pigment | 5 | 5 | 5 | 5 | 5 | 5 | 5 | 5 | 5 |

TABLE 11-continued

| | Test Example | | | | | | | | |
|---|---|---|---|---|---|---|---|---|---|
| | 2-15 | 2-16 | 2-17 | 2-18 | 2-19 | 2-20 | 2-21 | 2-22 | 2-23 |
| Wax | | | | | | | | | |
| Ceresin wax | 15 | 15 | 15 | 15 | 15 | 15 | 15 | 15 | 15 |
| Spreadability | ○ | ○ | ◉ | ◉ | ◉ | ○ | ○ | ○ | Δ |
| Luster | ○ | ○ | ○ | ○ | ○ | ○ | Δ | X | X |
| Secondary adhesion | ◉ | ◉ | ◉ | ◉ | ◉ | ◉ | ◉ | ◉ | ◉ |
| Stickiness | Δ | ○ | ◉ | ◉ | ◉ | ◉ | ◉ | ◉ | ◉ |

As can be seen from the above results, in order to improve the stickiness, the amount of silica is preferably 1.0% by weight or more. When the amount of silica exceeds 10% by weight, however, the feel of use such as spreadability may become worse while luster may somewhat deteriorate. Accordingly, in order to suppress the stickiness while maintaining luster, the amount of the powder is preferably 1.0 to 10% by weight and, particularly, 1.0 to 8.0% by weight. Here, when powders such as pigments are used in addition to silica, the total amount of these powders including silica is desirably 20% by weight or less.

Ratio of Oil Content to Polymer

It has been found that the ratio of the amount of the nonvolatile oil content to the water-repellent polymer greatly influences the improvement in feel of use and secondary adhesion also in this configuration, and further studies have been conducted.

The compositions and results are shown in Table-12.

TABLE 12

| | Test Example | | | | | | | |
|---|---|---|---|---|---|---|---|---|
| | 2-24 | 2-25 | 2-26 | 2-27 | 2-28 | 2-29 | 2-30 | 2-31 |
| Nonvolatile Oil Content | | | | | | | | |
| Liquid paraffin | 5 | 10 | 14.9 | 19.8 | 24.7 | 29.5 | 34.3 | 39.0 |
| Castor oil | — | — | 0.1 | 0.2 | 0.3 | 0.5 | 0.7 | 1.0 |
| Volatile Oil Content | | | | | | | | |
| Octamethyl-cyclotetra-siloxane | 30 | 30 | 30 | 30 | 30 | 30 | 30 | 30 |
| Polymer | | | | | | | | |
| Silicone resin A | 40 | 35 | 30 | 25 | 20 | 15 | 10 | 5 |
| Powder | | | | | | | | |
| Silica (Particle size 0.02 μm) | 5 | 5 | 5 | 5 | 5 | 5 | 5 | 5 |
| Pigment (Particle size 5 μm) | 5 | 5 | 5 | 5 | 5 | 5 | 5 | 5 |
| Wax | | | | | | | | |
| Ceresin wax | 15 | 15 | 15 | 15 | 15 | 15 | 15 | 15 |
| Resin/Nonvolatile Oil | 8/1 | 7/2 | 2/1 | 5/4 | 4/5 | 1/2 | 2/7 | 1/8 |
| Spreadability | X | Δ | ○ | ○ | ○ | ○ | ○ | ○ |
| Luster | Δ | Δ | ○ | ○ | ○ | ○ | ○ | ○ |
| Secondary adhesion | X | Δ | ◉ | ◉ | ◉ | ○ | Δ | X |
| Stickiness | X | Δ | ○ | ◉ | ◉ | ◉ | ◉ | ◉ |

As can be seen from the above results, when the ratio of the resin to the nonvolatile oil content exceeds 2/1, spreadability and luster deteriorate, while no considerable improvement in the secondary adhesion and stickiness is observed. When the ratio of the resin to the nonvolatile oil content is less than 1/2, the characteristic of the resin cannot be exhibited sufficiently, whereby the effect for improving the secondary adhesion may become insufficient.

Accordingly, the ratio of the resin to the nonvolatile oil content is preferably at least 1/2 but not more than 2/1.

(3) Correlation With Compounding Of Titanated Mica

First, the inventors prepared the lipsticks listed in the following and studied their feel of use, secondary adhesion, and the like. Here, in each of the test examples hereinafter, a small amount of a surface active agent is used. The compositions and results are shown in Table-13.

TABLE 13

| | Test Example | | | | |
|---|---|---|---|---|---|
| | 3-1 | 3-2 | 3-3 | 3-4 | 3-5 |
| Volatile Oil Content | | | | | |
| Octamethylcyclotetrasiloxane | 35 | 30 | 30 | 30 | 30 |
| Nonvolatile Oil Content | | | | | |
| Liquid paraffin | 20 | 20 | 20 | 20 | 20 |
| Polymer | | | | | |
| Silicone resin A | 25 | 25 | 25 | 25 | 25 |
| Powder | | | | | |
| Titanium oxide | — | 5 | — | 2 | — |
| Mica | — | — | 5 | 3 | — |
| Titanated mica A | — | — | — | — | 5 |
| Pigment | 5 | 5 | 5 | 5 | 5 |
| Wax | | | | | |
| Ceresin wax | 15 | 15 | 15 | 15 | 15 |
| Spreadability | ○ | ○ | ○ | ○ | ◉ |
| Luster | ○ | Δ | Δ | Δ | ◉ |
| Secondary adhesion | X | Δ | Δ | Δ | ◉ |
| Stickiness | X | Δ | Δ | Δ | ◉ |

Here, as titanated mica A, that with mica:$TiO_2$=60:40 was used.

As can be seen from the above results, no improvement in secondary adhesion is observed at all and stickiness occurs in the lipstick containing no powder at all (Test Example 3-1). Also, the improvement in luster, secondary adhesion, and stickiness is insufficient in the lipsticks compounded with titanium alone (Test Example 3-2) and mica alone (Test Example 3-3). Also, there is no luster, while improvement in secondary adhesion and stickiness is insufficient, in the lipstick (Test Example 3-4) in which titanium and mica are compounded with their ratio being the same as that in titanated mica A.

In Test Example 3-5 in which titanated mica A was compounded, a composition for lipstick in which each of luster, secondary adhesion, and stickiness was improved could be obtained.

Next, the inventors studied the effective amount of each ingredient.

Amount Of Water-Repellent Polymer

First, the inventors studied the amount of the water-repellent polymer. The compositions and results are shown in Table-14.

TABLE 14

|  | Test Example | | | | | | | |
|---|---|---|---|---|---|---|---|---|
|  | 3-6 | 3-7 | 3-8 | 3-9 | 3-10 | 3-11 | 3-12 | 3-13 |
| Volatile Oil Content | | | | | | | | |
| Octamethylcyclotetra-siloxane | 50 | 45 | 40 | 35 | 30 | 25 | 20 | 15 |
| Nonvolatile Oil Content | | | | | | | | |
| Liquid paraffin Polymer | 20 | 20 | 20 | 20 | 20 | 20 | 20 | 20 |
| Silicone resin A Powder | 5 | 10 | 15 | 20 | 25 | 30 | 35 | 40 |
| Titanated mica A | 5 | 5 | 5 | 5 | 5 | 5 | 5 | 5 |
| Pigment Wax | 5 | 5 | 5 | 5 | 5 | 5 | 5 | 5 |
| Ceresin wax | 15 | 15 | 15 | 15 | 15 | 15 | 15 | 15 |
| Spreadability | ○ | ○ | ○ | ◎ | ◎ | ◎ | ○ | △ |
| Luster | ○ | ○ | ○ | ◎ | ◎ | ◎ | ○ | ○ |
| Secondary adhesion | △ | ○ | ◎ | ◎ | ◎ | ◎ | ◎ | ◎ |
| Stickiness | ◎ | ◎ | ◎ | ◎ | ◎ | ◎ | ○ | △ |

As can be seen from the above results, in order to improve the secondary adhesion, the water-repellent polymer is preferably 10% by weight or more. When the water-repellent polymer exceeds 35% by weight, however, stickiness may occur or spreadability may deteriorate. Accordingly, it more preferably does not exceed 30% by weight.

Amount Of Powder

Next, the inventors studied the amount of the powder. The compositions and results are shown in Table-15.

TABLE 15

|  | Test Example | | | | | | |
|---|---|---|---|---|---|---|---|
|  | 3-14 | 3-15 | 3-16 | 3-17 | 3-18 | 3-19 | 3-20 |
| Volatile Oil Content | | | | | | | |
| Octamethylcyclotetra-siloxane | 35 | 34 | 33 | 30 | 27 | 25 | 20 |
| Nonvolatile Oil Content | | | | | | | |
| Liquid paraffin Polymer | 20 | 20 | 20 | 20 | 20 | 20 | 20 |
| Silicone resin A Powder | 25 | 25 | 25 | 25 | 25 | 25 | 25 |
| Titanated mica A | 0 | 1 | 2 | 5 | 8 | 10 | 15 |
| Pigment Wax | 5 | 5 | 5 | 5 | 5 | 5 | 5 |
| Ceresin wax | 15 | 15 | 15 | 15 | 15 | 15 | 15 |
| Spreadability | ○ | ○ | ◎ | ◎ | ◎ | ○ | ○ |
| Luster | ◎ | ◎ | ◎ | ◎ | ○ | ○ | △ |
| Secondary adhesion | △ | ○ | ◎ | ◎ | ◎ | ◎ | ◎ |
| Stickiness | △ | ○ | ◎ | ◎ | ◎ | ◎ | ◎ |

As can be seen from the above results, in order to improve the stickiness, the amount of titanated mica is preferably 1% by weight or more. When the amount of titanated mica exceeds 10% by weight, however, the feel of use such as spreadability may become worse while luster may somewhat deteriorate. Accordingly, in order to suppress the stickiness while maintaining luster, the amount of titanated mica is preferably 1 to 10% by weight and, particularly, 1 to 8% by weight. Here, when powders such as pigments are used in addition to titanated mica, the total amount of these powders including titanated mica is desirably 20% by weight or less.

Amount Of Nonvolatile Oil Content

Next, the amount of the nonvolatile oil content was studied. The compositions and results are shown in Table-16.

TABLE 16

|  | Test Example | | | | | | | | |
|---|---|---|---|---|---|---|---|---|---|
|  | 3-21 | 3-22 | 3-23 | 3-24 | 3-25 | 3-26 | 3-27 | 3-28 | 3-29 |
| Volatile Oil Content | | | | | | | | | |
| Octamethylcyclotetrasiloxane | 50 | 45 | 40 | 35 | 30 | 25 | 20 | 15 | 10 |
| Nonvolatile Oil Content | | | | | | | | | |
| Liquid paraffin Polymer | 5 | 10 | 15 | 20 | 25 | 30 | 35 | 40 | 45 |
| Silicone resin A Powder | 25 | 25 | 25 | 25 | 25 | 25 | 25 | 25 | 25 |
| Titanated mica A | 5 | 5 | 5 | 5 | 5 | 5 | 5 | 5 | 5 |
| Pigment Wax | 5 | 5 | 5 | 5 | 5 | 5 | 5 | 5 | 5 |
| Ceresin wax | 10 | 10 | 10 | 10 | 10 | 10 | 10 | 10 | 10 |
| Spreadability | ○ | ○ | ◎ | ◎ | ◎ | ○ | ○ | ○ | ○ |
| Luster | ◎ | ◎ | ◎ | ◎ | ◎ | ◎ | ◎ | ◎ | ◎ |
| Secondary adhesion | △ | ○ | ◎ | ◎ | ◎ | ◎ | ◎ | ○ | △ |
| Stickiness | △ | ○ | ◎ | ◎ | ◎ | ◎ | ◎ | ○ | ○ |

As can be seen from the above results, when the nonvolatile oil content is 10% by weight or less, the improvement in the secondary adhesion is insufficient, while stickiness occurs. When the nonvolatile oil content exceeds 40% by weight, on the other hand, the improvement in the secondary adhesion is not sufficient. Accordingly, the amount of the nonvolatile oil content is preferably 10 to 40% by weight.

Amount Ratio of Titanated Mica To Water-Repellent Polymer

Next, the amount ratio of titanated mica to the water-repellent polymer was studied. The compositions and results are shown in Table-17.

TABLE 17

| | Test Example | | | | | | | |
|---|---|---|---|---|---|---|---|---|
| | 3-30 | 3-31 | 3-32 | 3-33 | 3-34 | 3-35 | 3-36 | 3-37 |
| Volatile Oil Content | | | | | | | | |
| Octamethyl-cyclotetra-siloxane Nonvolatile Oil Content | 40 | 37.5 | 40 | 35 | 32 | 28 | 29 | 24 |
| Liquid paraffin Polymer | 20 | 20 | 20 | 20 | 20 | 20 | 20 | 20 |
| Silicone resin A Powder | 10 | 15 | 15 | 20 | 25 | 30 | 30 | 35 |
| Titanated mica A | 10 | 7.5 | 5 | 5 | 3 | 2 | 1 | 1 |
| Pigment | 5 | 5 | 5 | 5 | 5 | 5 | 5 | 5 |
| Wax | | | | | | | | |
| Ceresin wax | 15 | 15 | 15 | 15 | 15 | 15 | 15 | 15 |
| Titanated mica/Silicone resin | 1/1 | 1/2 | 1/3 | 1/4 | 3/25 | 1/15 | 1/30 | 1/35 |
| Spreadability | X | Δ | ○ | ◎ | ◎ | ◎ | ◎ | ◎ |
| Luster | Δ | ○ | ○ | ◎ | ◎ | ◎ | ◎ | ◎ |
| Secondary adhesion | ◎ | ◎ | ◎ | ◎ | ◎ | ○ | ○ | Δ |
| Stickiness | ◎ | ◎ | ◎ | ◎ | ◎ | ○ | ○ | Δ |

As can be seen from the above results, when the amount ratio of titanated mica to the silicone resin exceeds 1/2, the spreadability deteriorates and usability becomes inferior. At 1/35, however, stickiness occurs. Accordingly, the amount ratio of titanated mica to the silicone resin is preferably 1/30 to 1/3. Further, when the amount ratio of titanated mica to the silicone resin is 1/10 to 1/4, a rouge for lip which is excellent in all the usabilities can be obtained.

(4) Correlation With Combination Of Ultrafine Particle And Large-Size Particle

Next, the inventors prepared lipsticks with the following compositions and studied their feel of use, secondary adhesion, and the like. Here, in each of the following test examples, a small amount of a surface active agent is used. The ratio in particle size of the ultrafine particle to the large-size particle (referred to as "particle size ratio" hereinafter) was determined as the particle size of the ultrafine particle/particle size of the large-size particle. The compositions and results are shown in Table-18.

TABLE 18

| | Test Example | | | | | | | |
|---|---|---|---|---|---|---|---|---|
| | 4-1 | 4-2 | 4-3 | 4-4 | 4-5 | 4-6 | 4-7 | 4-8 |
| Nonvolatile Oil Content | | | | | | | | |
| Liquid paraffin Volatile Oil Content | 20 | 20 | 20 | 20 | 20 | 20 | 20 | 20 |
| Octamethylcyclo-tetrasiloxane Polymer | 60 | 60 | 60 | 60 | 60 | 60 | 60 | 60 |
| Silicone resin A Powder | 25 | 25 | 25 | 25 | 25 | 25 | 25 | 25 |
| Silica (Particle size 0.02 μm) | — | — | — | 5 | 5 | 5 | 5 | 5 |
| Silica (Particle size 2 μm) | — | — | 5 | — | — | — | — | — |
| Mica (Particle size 3 μm) | — | 10 | — | — | — | — | — | 10 |
| Pigment (Particle size 7 μm) | — | — | — | — | — | — | 5 | — |
| Pigment (Particle size 2 μm) | — | — | — | — | — | 5 | — | — |
| Pigment (Particle size 0.5 μm) | — | — | — | — | 5 | — | — | — |
| Wax | | | | | | | | |
| Ceresin wax | 15 | 15 | 15 | 15 | 15 | 15 | 15 | 15 |
| Particle size ratio | — | — | — | — | 0.04 | 0.01 | 0.003 | 0.007 |
| Spreadability | ○ | ○ | ○ | ○ | ○ | ○ | ○ | ○ |
| Luster | ◎ | Δ | Δ | Δ | ◎ | ○ | ○ | ○ |
| Secondary adhesion | X | Δ | Δ | ○ | ○ | ○ | ○ | ○ |
| Stickiness | X | Δ | Δ | Δ | ○ | ○ | ○ | ○ |

As can be seen from the above results, when no powder is compounded at all, no improvement in the secondary adhesion and stickiness is observed at all. Also, when a powder with a large particle size is compounded alone, the secondary adhesion cannot be improved sufficiently. When ultrafine silica is compounded, on the other hand, improvement is insufficient in terms of luster and stickiness.

Therefore, when various large-size particles were compounded together with ultrafine silica, a composition which was excellent in all the aspects of secondary adhesion, stickiness, and luster could be obtained.

Next, the inventors studied the effective amount of each ingredient.

Amount Of Water-Repellent Polymer

First, the inventors studied the amount of the water-repellent polymer. Here, the particle size ratio of the ultrafine particle to the large-size particle is 0.004. The compositions and results are shown in Table-19.

TABLE 19

| | Test Example | | | | | | | |
|---|---|---|---|---|---|---|---|---|
| | 4-9 | 4-10 | 4-11 | 4-12 | 4-13 | 4-14 | 4-15 | 4-16 |
| Nonvolatile Oil Content | | | | | | | | |
| Liquid paraffin Volatile Oil Content | 20 | 20 | 20 | 20 | 20 | 20 | 20 | 20 |
| Octamethylcyclo-tetrasiloxane | 50 | 45 | 40 | 35 | 30 | 25 | 20 | 15 |

TABLE 19-continued

| | Test Example | | | | | | | |
|---|---|---|---|---|---|---|---|---|
| | 4-9 | 4-10 | 4-11 | 4-12 | 4-13 | 4-14 | 4-15 | 4-16 |
| Polymer | | | | | | | | |
| Silicone resin A Powder | 5 | 10 | 15 | 20 | 25 | 30 | 35 | 40 |
| Silica (Particle size 0.02 μm) | 5 | 5 | 5 | 5 | 5 | 5 | 5 | 5 |
| Pigment (Particle size 5 μm) | 5 | 5 | 5 | 5 | 5 | 5 | 5 | 5 |
| Wax | | | | | | | | |
| Ceresin wax | 15 | 15 | 15 | 15 | 15 | 15 | 15 | 15 |
| Spreadability | ○ | ○ | ○ | ○ | ○ | ○ | ○ | ○ |
| Luster | ○ | ○ | ○ | ○ | ○ | ○ | ○ | ○ |
| Second adhesion | △ | ○ | ◎ | ◎ | ◎ | ◎ | ○ | X |
| Stickiness | ◎ | ◎ | ◎ | ◎ | ◎ | ◎ | ○ | ○ |

As can be seen from the above results, in order to improve the secondary adhesion, the water-repellent polymer is preferably 10% by weight or more and, more preferably, 15% by weight or more. When the water-repellent polymer exceeds 35% by weight, however, stickiness may occur or spreadability may deteriorate. Accordingly, it more preferably does not exceed 30% by weight.

Amount Of Powder

Next, the inventors studied the amount of the powder. First, the amount of the ultrafine particle was studied. The compositions and results are shown in Table-20.

TABLE 20

| | Test Example | | | | | | | |
|---|---|---|---|---|---|---|---|---|
| | 4-17 | 4-18 | 4-19 | 4-20 | 4-21 | 4-22 | 4-23 | 4-24 |
| Nonvolatile Oil Content | | | | | | | | |
| Liquid paraffin Volatile Oil Content | 20 | 20 | 20 | 20 | 20 | 20 | 20 | 20 |
| Octamethyl-cyclotetra-siloxane Polymer | 39.5 | 39.0 | 38.0 | 35.0 | 32.0 | 30.0 | 25.0 | 20.0 |
| Silicone resin A Powder | 20 | 20 | 20 | 20 | 20 | 20 | 20 | 20 |
| Silica (Particle size 0.02 μm) | 0.5 | 1.0 | 2.0 | 5.0 | 8.0 | 10.0 | 15.0 | 20.0 |
| Pigment (Particle size 5 μm) | 5 | 5 | 5 | 5 | 5 | 5 | 5 | 5 |
| Wax | | | | | | | | |
| Ceresin wax | 15 | 15 | 15 | 15 | 15 | 15 | 15 | 15 |
| Spreadability | ◎ | ◎ | ◎ | ◎ | ○ | ○ | X | X |
| Luster | ○ | ○ | ○ | ○ | ○ | ○ | △ | X |
| Secondary adhesion | ○ | ○ | ◎ | ◎ | ◎ | ◎ | ◎ | ◎ |
| Stickiness | △ | ○ | ◎ | ◎ | ◎ | ◎ | ◎ | ◎ |

As can be seen from the above results, in order to improve the stickiness, the amount of silica is preferably 1% by weight or more. When the amount of silica exceeds 10% by weight, however, the feel of use such as spreadability may become worse while luster may somewhat deteriorate. Accordingly, in order to suppress the stickiness while maintaining luster, the amount of silica is preferably 1 to 10% by weight and, particularly, 1 to 8% by weight.

Further, the compounding ratio of the ultrafine particle to the large-size particle was studied. Here, the particle size ratio is 0.004 in this test. The compositions and results are shown in Table-21.

TABLE 21

| | Test Example | | | | | | | |
|---|---|---|---|---|---|---|---|---|
| | 4-25 | 4-26 | 4-27 | 4-28 | 4-29 | 4-30 | 4-31 | 4-32 |
| Nonvolatile Oil Content | | | | | | | | |
| Liquid paraffin Volatile Oil Content | 20 | 20 | 20 | 20 | 20 | 20 | 20 | 20 |
| Octamethyl-cyclotetra-siloxane Polymer | 24 | 25 | 25 | 25 | 25 | 25 | 30 | 34 |
| Silicone resin A Powder | 25 | 25 | 25 | 25 | 25 | 25 | 25 | 25 |
| Silica (Particle size 0.02 μm) | 1.0 | 2.0 | 3.0 | 5.0 | 8.0 | 10.0 | 10.0 | 10.0 |
| Pigment (Particle size 5 μm) | 19.0 | 18.0 | 17.0 | 15.0 | 12.0 | 10.0 | 5.0 | 1.0 |
| Wax | | | | | | | | |
| Ceresin wax | 10 | 10 | 10 | 10 | 10 | 10 | 10 | 10 |
| Ultrafine particle/ Large-size particle | 1/19 | 1/9 | 3/17 | 1/3 | 2/3 | 1/1 | 2/1 | 10/1 |
| Spreadability | ◎ | ◎ | ◎ | ◎ | ○ | ○ | ○ | ○ |
| Luster | ○ | ○ | ○ | ◎ | ◎ | ○ | ○ | ○ |
| Secondary adhesion | ○ | ○ | ◎ | ◎ | ◎ | ◎ | ◎ | ◎ |
| Stickiness | ○ | ◎ | ◎ | ◎ | ◎ | ◎ | ◎ | ◎ |

As can be seen from the above results, when the compounding ratio of the ultrafine particle to the large-size particle is 1:19 to 10:1, a composition with improved feel of use and secondary adhesion can be obtained.

Ratio Of Oil Content To Water-Repellent Polymer

It has been found that the ratio of the amount of the nonvolatile oil content to the water-repellent polymer greatly influences the improvement in feel of use and secondary adhesion also in this configuration, and further studies have been conducted. The compositions and results are shown in Table-22.

TABLE 22

| | Test Example | | | | | | | |
|---|---|---|---|---|---|---|---|---|
| | 4-33 | 4-34 | 4-35 | 4-36 | 4-37 | 4-38 | 4-39 | 4-40 |
| Nonvolatile Oil Content | | | | | | | | |
| Liquid paraffin | 5 | 10 | 14.9 | 19.8 | 24.7 | 29.5 | 34.3 | 39.0 |
| Castor oil Volatile Oil Content | — | — | 0.1 | 0.2 | 0.3 | 0.5 | 0.7 | 1.0 |
| Octamethyl-cyclotetra- | 30 | 30 | 30 | 30 | 30 | 30 | 30 | 30 |

TABLE 22-continued

| | Test Example | | | | | | | |
|---|---|---|---|---|---|---|---|---|
| | 4-33 | 4-34 | 4-35 | 4-36 | 4-37 | 4-38 | 4-39 | 4-40 |
| siloxane Polymer | | | | | | | | |
| Silicone resin A Powder | 40 | 35 | 30 | 25 | 20 | 15 | 10 | 5 |
| Silica (Particle size 0.02 µm) | 5 | 5 | 5 | 5 | 5 | 5 | 5 | 5 |
| Pigment (Particle size 5 µm) | 5 | 5 | 5 | 5 | 5 | 5 | 5 | 5 |
| Wax | | | | | | | | |
| Ceresin wax | 15 | 15 | 15 | 15 | 15 | 15 | 15 | 15 |
| Resin/Nonvolatile Oil Content | 8/1 | 7/2 | 2/1 | 5/4 | 4/5 | 1/2 | 2/7 | 1/8 |
| Spreadability | X | Δ | ◯ | ◯ | ◯ | ◯ | ◯ | ◯ |
| Luster | Δ | Δ | ◯ | ◯ | ◯ | ◯ | ◯ | ◯ |
| Secondary adhesion | X | Δ | ◉ | ◉ | ◉ | ◯ | Δ | X |
| Stickiness | X | Δ | ◯ | ◉ | ◉ | ◉ | ◉ | ◉ |

As can be seen from the above results, when the ratio of the resin to the nonvolatile oil content exceeds 2/1, spreadability and luster deteriorate, while no considerable improvement in secondary adhesion and stickiness is observed. When the ratio of the resin to the nonvolatile oil content is less than 1/2, the characteristic of the resin cannot be exhibited sufficiently, whereby the effect for improving the secondary adhesion may become insufficient.

Accordingly, the ratio of the resin to the nonvolatile oil content is preferably at least 1/2 but not more than 2/1.

(5) Correlation With Turbidity Of Water-Repellent Polymer And Nonvolatile Oil Content The inventors have found that, even when the powder is not an essential constituent, the state of existence of the nonvolatile oil content and water-repellent polymer after the volatilization of the volatile oil content greatly influences the feel of use and the secondary adhesion.

Namely, it seems that, as the nonvolatile oil content remaining on the lip after the volatilization of the volatile oil content appropriately plasticizes the water-repellent polymer, wetness is rendered to the lip after the application, in addition to the improvement in feel of use and secondary adhesion.

Prior to the studies, the method of measuring turbidity will be explained.

[Method of Measuring Turbidity]

1. A mixed sample is prepared as a volatile oil content, a water-repellent polymer, and a nonvolatile oil content are mixed together with their respective ratios identical to those in the composition.

2. Into a middle-sized black dish of 2.8×1.9×0.3 cm³, 0.2 g of the above-mentioned mixed sample is poured and then left for 6 hours at 90° C. so as to completely volatilize the volatile oil content.

3. The turbidity of thus obtained sample is measured by a colorimeter (Color-Eye7000, manufactured by Macbeth Co.; the measured L value being defined as the turbidity).

In view of the above findings, the turbidity of the water-repellent polymer and nonvolatile oil content was studied. Here, in each of the following test examples, a small amount of a surface active agent is used. The compositions and results are shown in Table-23.

TABLE 23

| | Test Example | | | | | | | | | |
|---|---|---|---|---|---|---|---|---|---|---|
| | 5-1 | 5-2 | 5-3 | 5-4 | 5-5 | 5-6 | 5-7 | 5-8 | 5-9 | 5-10 |
| Volatile Oil Content | | | | | | | | | | |
| Octamethylcyclotetrasiloxane | 50 | 45 | 40 | 35 | 30 | 25 | 20 | 15 | 10 | 5 |
| Nonvolatile Oil Content | | | | | | | | | | |
| Liquid paraffin | 0 | 5 | 10 | 15 | 20 | 25 | 30 | 35 | 40 | 45 |
| Polymer | | | | | | | | | | |
| Silicone resin A Powder | 25 | 25 | 25 | 25 | 25 | 25 | 25 | 25 | 25 | 25 |
| Silica | 5 | 5 | 5 | 5 | 5 | 5 | 5 | 5 | 5 | 5 |
| Pigment | 5 | 5 | 5 | 5 | 5 | 5 | 5 | 5 | 5 | 5 |
| Wax | | | | | | | | | | |
| Ceresin wax | 15 | 15 | 15 | 15 | 15 | 15 | 15 | 15 | 15 | 15 |
| Turbidity | 28.9 | 25.6 | 18.3 | 15.2 | 13.8 | 11.9 | 10.3 | 9.5 | 8.9 | 8.1 |
| Spreadability | X | Δ | ◯ | ◯ | ◯ | ◯ | ◯ | ◯ | ◉ | ◉ |
| Luster | Δ | Δ | ◯ | ◯ | ◯ | ◯ | ◯ | ◯ | ◯ | ◯ |
| Secondary adhesion | X | ◯ | ◉ | ◉ | ◉ | ◉ | ◯ | ◯ | Δ | X |
| Stickiness | X | X | ◯ | ◉ | ◉ | ◉ | ◉ | ◉ | ◉ | ◉ |

As can be seen from the above results, when the turbidity is 25.6 or more, there occur spreadability, luster, secondary adhesion, and stickiness. When the turbidity is 8.9 or less, on the other hand, the characteristic of the resin cannot be exhibited sufficiently, whereby the effect for improving the secondary adhesion may become insufficient.

Also, the inventors adjusted the turbidity by using, of the nonvolatile oil content, oil contents having different plasticizing capacities with respect to the water-repellent polymer so as to further conduct studies. The compositions and results are shown in Table-24.

TABLE 24

| | Test Example | | | | | | | |
|---|---|---|---|---|---|---|---|---|
| | 5-11 | 5-12 | 5-13 | 5-14 | 5-15 | 5-16 | 5-17 | 5-18 |
| Volatile Oil Content | | | | | | | | |
| Octamethyl-cyclotetra-siloxane | 35 | 31.5 | 29.0 | 25.5 | 23.0 | 19.5 | 17.0 | 13.5 |
| Nonvolatile Oil Content | | | | | | | | |
| Liquid paraffin | 15 | 18 | 20 | 23 | 25 | 28 | 30 | 33 |
| Castor oil | — | 0.5 | 1.0 | 1.5 | 2.0 | 2.5 | 3.0 | 3.5 |
| Polymer | | | | | | | | |
| Silicone resin A | 25 | 25 | 25 | 25 | 25 | 25 | 25 | 25 |
| Powder | | | | | | | | |
| Silica | 5 | 5 | 5 | 5 | 5 | 5 | 5 | 5 |
| Pigment | 5 | 5 | 5 | 5 | 5 | 5 | 5 | 5 |
| Wax | | | | | | | | |
| Ceresin wax | 15 | 15 | 15 | 15 | 15 | 15 | 15 | 15 |
| Turbidity | 15.2 | 14.8 | 14.4 | 14.1 | 13.6 | 12.9 | 11.8 | 11.1 |
| Spreadability | ○ | ○ | ○ | ○ | ○ | ○ | ○ | ○ |
| Luster | ○ | ○ | ○ | ○ | ○ | ○ | ○ | ○ |
| Secondary adhesion | ◎ | ◎ | ◎ | ◎ | ◎ | ◎ | ○ | ○ |
| Stickiness | ◎ | ◎ | ◎ | ◎ | ◎ | ◎ | ◎ | ◎ |

As can be seen from the above results, when, of the nonvolatile oil content, an oil content having a high plasticizing capacity and an oil content having a low plasticizing capacity with respect to the water-repellent polymer are combined together so as to attain an appropriate turbidity, a composition having favorable conformability and improved secondary adhesion can be obtained. Namely, in the present invention, when the amounts of the nonvolatile oil contents having different plasticizing capacities are adjusted, the turbidity of the water-repellent polymer and nonvolatile oil content can be adjusted.

Further, while the amount of the resin is set at 15% by weight and 35% by weight, the nonvolatile oil content was adjusted and evaluated. The compositions and results are shown in Table-25.

TABLE 25

| | Test Example | | | | | | | |
|---|---|---|---|---|---|---|---|---|
| | 5-19 | 5-20 | 5-21 | 5-22 | 5-23 | 5-24 | 5-25 | 5-26 |
| Volatile Oil Content | | | | | | | | |
| Octamethyl-cyclotetra-siloxane | 52 | 40 | 29 | 37 | 27 | 21.8 | 16.5 | 19 |
| Nonvolatile Oil Content | | | | | | | | |
| Trimethylol-propane tri-2-ethyl hexanoate | — | — | — | 20 | — | — | — | 25 |
| Liquid paraffin | 10 | 20 | 30 | — | 20 | 25 | 30 | — |
| Castor oil | — | 2 | 3 | 5 | — | 0.2 | 0.5 | 3 |
| Polymer | | | | | | | | |
| Silicone resin A | 15 | 15 | 15 | 15 | 35 | 35 | 35 | 35 |
| Powder | | | | | | | | |
| Silica | 3 | 3 | 3 | 3 | 3 | 3 | 3 | 3 |
| Pigment | 5 | 5 | 5 | 5 | 5 | 5 | 5 | 5 |
| Wax | | | | | | | | |
| Ceresin wax | 15 | 15 | 15 | 15 | 10 | 10 | 10 | 10 |
| Turbidity | 13.1 | 12.0 | 9.1 | 12.1 | 21.6 | 19.3 | 17.7 | 14.1 |
| Spreadability | ○ | ○ | ○ | ○ | ○ | ○ | ○ | ○ |
| Luster | ○ | ○ | ○ | ○ | ○ | ○ | ○ | ○ |
| Secondary adhesion | ◎ | ○ | ○ | ◎ | ◎ | ◎ | ◎ | ◎ |
| Stickiness | ○ | ○ | ◎ | ○ | ○ | ○ | ◎ | ○ |

As can be seen from the above results, when the composition of the nonvolatile oil content to be compounded is changed, while the amount of resin is held constant, to adjust the turbidity, a composition for rouge for lip having favorable spreadability, improved secondary adhesion, and no stickiness can be obtained.

Accordingly, in the composition for rouge for lip in the present invention, the turbidity of the water-repellent polymer and nonvolatile oil content is preferably at least 9.0 but not more than 25.5.

Next, the inventors studied the effective amount of each ingredient.

Amount Of Water-Repellent Polymer

First, the inventors studied the amount of the water-repellent polymer. The compositions and results are shown in Table-26.

TABLE 26

| | Test Example | | | | | | | |
|---|---|---|---|---|---|---|---|---|
| | 5-27 | 5-28 | 5-29 | 5-30 | 5-31 | 5-32 | 5-33 | 5-34 |
| Volatile Oil Content | | | | | | | | |
| Octamethyl-cyclotetra-siloxane | 48 | 43 | 38 | 33 | 28 | 23 | 18 | 13 |
| Nonvolatile Oil Content | | | | | | | | |
| Liquid paraffin | 20 | 20 | 20 | 20 | 20 | 20 | 20 | 20 |
| Castor oil | 2 | 2 | 2 | 2 | 2 | 2 | 2 | 2 |
| Polymer | | | | | | | | |
| Silicone resin A | 5 | 10 | 15 | 20 | 25 | 30 | 35 | 40 |
| Powder | | | | | | | | |
| Silica | 5 | 5 | 5 | 5 | 5 | 5 | 5 | 5 |
| Pigment | 5 | 5 | 5 | 5 | 5 | 5 | 5 | 5 |
| Wax | | | | | | | | |
| Ceresin wax | 15 | 15 | 15 | 15 | 15 | 15 | 15 | 15 |
| Turbidity | 9.1 | 10.0 | 12.0 | 14.5 | 18.3 | 20.1 | 23.5 | 25.3 |
| Spreadability | ○ | ○ | ○ | ○ | ○ | ○ | ○ | △ |
| Luster | ○ | ○ | ○ | ○ | ○ | ○ | ○ | ○ |
| Secondary adhesion | △ | ○ | ◎ | ◎ | ◎ | ◎ | ◎ | ◎ |
| Stickiness | ◎ | ◎ | ◎ | ◎ | ◎ | ◎ | ○ | △ |

As can be seen from the above results, even when the turbidity is within the suitable range, in order to improve the secondary adhesion, the water-repellent polymer is preferably 10% by weight or more. When the water-repellent polymer exceeds 35% by weight, however, stickiness may occur or spreadability may deteriorate. Accordingly, it more preferably does not exceed 30% by weight.

Amount Of Powder

Next, the inventors studied the amount of the powder. The compositions and results are shown in Table-27.

TABLE 27

| | Test Example | | | | | | |
|---|---|---|---|---|---|---|---|
| | 5-35 | 5-36 | 5-37 | 5-38 | 5-39 | 5-40 | 5-41 |
| Volatile Oil Content | | | | | | | |
| Octamethylcyclotetrasiloxane | 34.8 | 34.7 | 33.8 | 28.8 | 25.8 | 23.8 | 18.8 |
| Nonvolatile Oil Content | | | | | | | |
| Liquid paraffin | 20 | 20 | 20 | 20 | 20 | 20 | 20 |
| Castor oil | 0.2 | 0.2 | 0.2 | 0.2 | 0.2 | 0.2 | 0.2 |
| Polymer | | | | | | | |
| Silicone resin A | 25 | 25 | 25 | 25 | 25 | 25 | 25 |
| Powder | | | | | | | |
| Silica | 0 | 0.1 | 1.0 | 5.0 | 8.0 | 10.0 | 15.0 |
| Pigment | 5 | 5 | 5 | 5 | 5 | 5 | 5 |
| Wax | | | | | | | |
| Ceresin wax | 15 | 15 | 15 | 15 | 15 | 15 | 15 |
| Turbidity | 13.1 | 13.1 | 13.1 | 13.1 | 13.1 | 13.1 | 13.1 |
| Spreadability | O | O | ⊚ | ⊚ | ⊚ | O | O |
| Luster | O | O | O | O | O | O | Δ |
| Secondary adhesion | Δ | O | ⊚ | ⊚ | ⊚ | ⊚ | ⊚ |
| Stickiness | Δ | O | ⊚ | ⊚ | ⊚ | ⊚ | ⊚ |

As can be seen from the above results, in order to improve the stickiness, the amount of silica is preferably 0.1% by weight or more. When the amount of silica exceeds 10% by weight, however, the feel of use such as spreadability may deteriorate. Accordingly, the amount of silica is preferably 0.1 to 10% by weight and, more preferably, 1 to 8% by weight. Here, when powders such as pigments are used in addition to silica, the total amount of these powders including silica is desirably 20% by weight or less.

(6) Correlation With Combination of Water-Repellent Polymer And Wax

Also, the inventors have found that, even in the case where the powder is not an essential constituent, the secondary adhesion and the feel of use can be improved when the water-repellent polymer and the wax have a predetermined compounding ratio.

Namely, the inventors prepared rouge for lip with the following compositions and studied their feel of use, secondary adhesion, and the like. Here, in each of the following test examples, a small amount of a surface active agent is used. The compositions and results are shown in Table-28.

TABLE 28

| | Test Example | | | | |
|---|---|---|---|---|---|
| | 6-1 | 6-2 | 6-3 | 6-4 | 6-5 |
| Nonvolatile Oil Content | | | | | |
| Liquid paraffin | 20 | 20 | 20 | 20 | 20 |
| Volatile Oil Content | | | | | |
| Octamethylcyclotetrasiloxane | 75 | 50 | 60 | 35 | 30 |

TABLE 28-continued

| | Test Example | | | | |
|---|---|---|---|---|---|
| | 6-1 | 6-2 | 6-3 | 6-4 | 6-5 |
| Polymer | | | | | |
| Silicone resin A | — | 25 | — | 25 | 25 |
| Wax | | | | | |
| Ceresin wax | — | — | 15 | 15 | 15 |
| Powder | | | | | |
| Silica | — | — | — | — | 5 |
| Pigment | 5 | 5 | 5 | 5 | 5 |
| Spreadability | ⊚ | ⊚ | ⊚ | ⊚ | ⊚ |
| Luster | ⊚ | Δ | Δ | O | ⊚ |
| Secondary adhesion | X | Δ | Δ | O | ⊚ |
| Stickiness | X | X | O | ⊚ | ⊚ |
| Powdery feel | O | O | X | ⊚ | ⊚ |

As can be seen from the above results, no improvement in the secondary adhesion can be seen in the rouge for lip formulated with the oil contents and pigment alone (Test Example 6-1). Then, when a rouge for lip compounded with a silicone resin was formulated, stickiness occurred while the secondary adhesion was slightly improved (Test Example 6-2). When a wax having a coat-forming capacity similar to that of the silicone resin is compounded, on the other hand, though without stickiness, powdery feel is generated with insufficient improvement in the secondary adhesion (Test Example 6-3). Then, when a rouge for lip in which the wax was compounded together with the silicone resin was formulated, it was found to be a rouge for lip excellent in all the sensory evaluations with improved secondary adhesion (Test Example 6-4). It is suggested that a rouge for lip in which silica is further compounded in the above-mentioned rouge for lip becomes a rouge for lip whose secondary adhesion is further improved (Test Example 6-5).

Compounding Ratio Of Water-Repellent Polymer To Wax

Next, the inventors studied the compounding ratio of the water-repellent polymer to the wax. The compositions and results are shown in Table-29.

TABLE 29

| | Test Example | | | | | |
|---|---|---|---|---|---|---|
| | 6-6 | 6-7 | 6-8 | 6-9 | 6-10 | 6-11 |
| Nonvolatile Oil Content | | | | | | |
| Liquid paraffin | 20 | 20 | 20 | 20 | 20 | 20 |
| Volatile Oil Content | | | | | | |
| Octamethylcyclotetrasiloxane | 35 | 36 | 37 | 38 | 39 | 40 |
| Polymer | | | | | | |
| Silicone resin A | 35 | 30 | 25 | 20 | 15 | 10 |
| Wax | | | | | | |
| Ceresin wax | 5 | 9 | 13 | 17 | 21 | 25 |
| Powder | | | | | | |
| Pigment | 5 | 5 | 5 | 5 | 5 | 5 |
| Silicone resin/Wax | 7/1 | 10/3 | 25/13 | 20/17 | 5/7 | 2/5 |
| Spreadability | O | O | O | O | O | O |
| Luster | O | O | O | O | O | O |
| Secondary adhesion | Δ | O | ⊚ | ⊚ | ⊚ | ⊚ |
| Stickiness | Δ | O | ⊚ | ⊚ | ⊚ | ⊚ |
| Powdery feel | O | O | ⊚ | ⊚ | ⊚ | Δ |

As can be seen from the above results, the improvement in secondary adhesion and stickiness is insufficient when the amount of silicone resin is large. When the amount of the wax is large, on the other hand, powdery feel occurs. Accordingly, the compounding ratio of the water-repellent polymer to the wax is preferably 10/3 to 5/7.

Next, the inventors studied the effective amount of each ingredient.

Amount Of Water-Repellent Polymer

First, the inventors studied the amount of the water-repellent polymer. The compositions and results are shown in Table-30.

TABLE 30

| | Test Example | | | | | | | |
|---|---|---|---|---|---|---|---|---|
| | 6-12 | 6-13 | 6-14 | 6-15 | 6-16 | 6-17 | 6-18 | 6-19 |
| Nonvolatile Oil Content | | | | | | | | |
| Liquid paraffin Volatile Oil Content | 20 | 20 | 20 | 20 | 20 | 20 | 20 | 20 |
| Octamethyl-cyclotetra-siloxane Polymer | 55 | 50 | 45 | 40 | 35 | 30 | 25 | 20 |
| Silicone resin A Wax | 5 | 10 | 15 | 20 | 25 | 30 | 35 | 40 |
| Ceresin wax Powder | 15 | 15 | 15 | 15 | 15 | 15 | 15 | 15 |
| Pigment | 5 | 5 | 5 | 5 | 5 | 5 | 5 | 5 |
| Spreadability | ○ | ○ | ○ | ○ | ○ | ○ | ○ | ○ |
| Luster | ○ | ○ | ○ | ○ | ○ | ○ | ○ | ○ |
| Secondary adhesion | Δ | ○ | ⊙ | ⊙ | ⊙ | ⊙ | ○ | Δ |
| Stickiness | ○ | ○ | ⊙ | ⊙ | ⊙ | ⊙ | ○ | Δ |
| Powdery feel | Δ | ○ | ⊙ | ⊙ | ⊙ | ⊙ | ⊙ | ⊙ |

As can be seen from the above results, when the water-repellent polymer is 10% by weight or less, improvement in the secondary adhesion may be insufficient while powdery feel may occur. Accordingly, in order to improve the secondary adhesion, the water-repellent polymer is preferably 10% by weight or more and, in particular, 15% by weight or more. When the water-repellent polymer exceeds 35% by weight, however, stickiness may occur and improvement in the second adhesion may become insufficient. Accordingly, it more preferably does not exceed 30% by weight.

Amount Of Wax

Next, the inventors studied the amount of the wax. The compositions and results are shown in Table-31

TABLE 31

| | Test Example | | | | | | | |
|---|---|---|---|---|---|---|---|---|
| | 6-20 | 6-21 | 6-22 | 6-23 | 6-24 | 6-25 | 6-26 | 6-27 |
| Nonvolatile Oil Content | | | | | | | | |
| Liquid paraffin Volatile Oil Content | 20 | 20 | 20 | 20 | 20 | 20 | 20 | 20 |
| Octamethyl- | 47 | 45 | 42 | 40 | 35 | 30 | 25 | 20 |

TABLE 31-continued

| | Test Example | | | | | | | |
|---|---|---|---|---|---|---|---|---|
| | 6-20 | 6-21 | 6-22 | 6-23 | 6-24 | 6-25 | 6-26 | 6-27 |
| cyclotetra-siloxane Polymer | | | | | | | | |
| Silicone resin A Wax | 25 | 25 | 25 | 25 | 25 | 25 | 25 | 25 |
| Ceresin wax Powder | 3 | 5 | 8 | 10 | 15 | 20 | 25 | 30 |
| Pigment | 5 | 5 | 5 | 5 | 5 | 5 | 5 | 5 |
| Spreadability | ○ | ○ | ○ | ○ | ○ | ○ | ○ | ○ |
| Luster | ○ | ○ | ○ | ○ | ○ | ○ | ○ | ○ |
| Secondary adhesion | Δ | ○ | ⊙ | ⊙ | ⊙ | ⊙ | ○ | Δ |
| Stickiness | Δ | Δ | ⊙ | ⊙ | ⊙ | ⊙ | ○ | ○ |
| Powdery feel | ○ | ○ | ⊙ | ⊙ | ⊙ | ⊙ | ⊙ | Δ |

As can be seen from the above results, in order to improve the secondary adhesion, the wax is preferably 5% by weight or more and, in particular, 8% by weight or more. When the wax exceeds 25% by weight, however, powdery feel occurs and improvement of the secondary adhesion is insufficient. Accordingly, it more preferably does not exceed 20% by weight.

Amount Of Powder

Next, the inventors studied the amount of the powder. The compositions and results are shown in Table-32.

TABLE 32

| | Test Example | | | | | | | |
|---|---|---|---|---|---|---|---|---|
| | 6-28 | 6-29 | 6-30 | 6-31 | 6-32 | 6-33 | 6-34 | 6-35 |
| Nonvolatile Oil Content | | | | | | | | |
| Liquid paraffin Volatile Oil Content | 20 | 20 | 20 | 20 | 20 | 20 | 20 | 20 |
| Octamethyl-cyclotetra-siloxane Polymer | 47 | 45 | 42 | 40 | 35 | 30 | 25 | 20 |
| Silicone resin A Wax | 25 | 25 | 25 | 25 | 25 | 25 | 25 | 25 |
| Ceresin wax Powder | 10 | 10 | 10 | 10 | 10 | 10 | 10 | 10 |
| Silica | 0 | 0.5 | 1 | 3 | 5 | 8 | 10 | 15 |
| Pigment | 5 | 5 | 5 | 5 | 5 | 5 | 5 | 5 |
| Spreadability | ○ | ○ | ○ | ○ | ○ | ○ | ○ | X |
| Luster | ⊙ | ⊙ | ⊙ | ⊙ | ⊙ | ⊙ | ○ | X |
| Secondary adhesion | ○ | ○ | ⊙ | ⊙ | ⊙ | ⊙ | ⊙ | ⊙ |
| Stickiness | ○ | ○ | ⊙ | ⊙ | ⊙ | ⊙ | ○ | ○ |
| Powdery feel | ○ | ○ | ⊙ | ⊙ | ⊙ | ⊙ | ⊙ | Δ |

As can be seen from the above results, luster of the rouge for lip increases as silica is compounded therein. When 1% by weight or more of silica is compounded, improvement in the secondary adhesion becomes strong. When the amount of silica exceeds 10% by weight, however, the feel of use such as spreadability may become worse while luster may deteriorate. Accordingly, in order to further strengthen the improvement in the secondary adhesion while maintaining the luster, the amount of silica is preferably 1 to 10% by weight inclusive and, in particular, 1 to 8% by weight.

(7) Correlation With Compounding Of Water

In the process of the foregoing studies, the inventors have found that, when water is compounded, a composition for rouge for lip with improved feel of use and ameliorated secondary adhesion can be obtained. Here, in each of the following test examples, a small amount of a surface active agent is used. The compositions and results are shown in Table-33.

TABLE 33

|  | Test Example | | | | |
|---|---|---|---|---|---|
|  | 7-1 | 7-2 | 7-3 | 7-4 | 7-5 |
| Nonvolatile Oil Content | | | | | |
| Glycerin diisostearate | 10 | 10 | 10 | 10 | 10 |
| Castor oil | 10 | 10 | 10 | 10 | 10 |
| Volatile Oil Content | | | | | |
| Octamethylcyclotetrasiloxane | 35 | 30 | 30 | 30 | 35 |
| Polymer | | | | | |
| Silicone resin A | 15 | 15 | 15 | 15 | 15 |
| Powder | | | | | |
| Silica | 5 | 5 | 5 | 5 | — |
| Pigment | 5 | 5 | 5 | 5 | 5 |
| Wax | | | | | |
| Ceresin wax | 15 | 15 | 15 | 15 | 15 |
| Emulsifier | | | | | |
| Polyether-denatured dimethylpolysiloxane | — | 1 | 1 | 1 | 1 |
| Synthetic hectorite | — | 3 | 3 | 3 | 3 |
| Water | | | | | |
| Natural water A | — | — | — | 1 | 1 |
| Ion-exchanged water | — | — | 1 | — | — |
| Service water | — | 1 | — | — | — |
| Spreadability | ○ | ○ | ○ | ○ | ○ |
| Luster | △ | ○ | ○ | ⊚ | ○ |
| Secondary adhesion | ⊚ | ⊚ | ⊚ | ⊚ | △ |
| Wetness | △ | △ | ○ | ⊚ | ⊚ |

Here, as the synthetic hectorite, that available from Laporte Industries Ltd. in the United Kingdom under the trademark of Laponite XLG was used. As natural water A, that collected at the foothills of Mount Fuji was used; as the tap water, that supplied from the water supply of Yokohama City was used; and, as the ion-changed water, the water supplied from the water supply of Yokohama City and then subjected to ion exchange was used.

As can be seen from the above results, wetness is lower in the composition in which no water is compounded. When water is compounded, on the other hand, luster is improved. Further, when natural water is compounded, a composition for rouge for lip excellent in both luster and wetness can be obtained. Since water does not improve the secondary adhesion, however, when silica which has been compounded in order to improve the secondary adhesion is eliminated, the improvement in the secondary adhesion which is the aimed object of the present invention cannot be attained, though luster and wetness remain.

Accordingly, it is suggested that, when water is added to each of the compositions for improving the secondary adhesion, a composition for rouge for lip whose secondary adhesion is improved and which is excellent in luster and wetness can be obtained.

In the following, preferable compounding examples of the present invention will be shown. In each example, the secondary adhesion was improved while no stickiness occurred. The amounts are indicated by % by weight unless otherwise indicated in particular.

1. Examples Of Total Surface Area Of Powders In Composition

Example 1-1 Lipstick

| | |
|---|---|
| Ceresin wax | 15.0 wt % |
| Carnauba wax | 2.0 |
| Glyceryl diisostearate | 15.0 |
| Lanoline | 0.2 |
| Macademia nut oil | 0.1 |
| Diisostearyl malate | 3.0 |
| Trimethylolpropane tri-2-ethyl hexanoate | 1.5 |
| Glyceryl triisostearate | 1.5 |
| Silicone resin which has a molecular weight of about 3,000 and is expressed by mean formula of $(CH_3)_{1.33}SiO_{1.34}$ with $(CH_3)_3SiO_{1/2}:SiO_2$ unit = 0.8:1 | 30.0 |
| Octamethylcyclotetrasiloxane | 21.7 |
| Silica (Specific surface area 200 $m^2/g$) | 5.0 |
| Pigment (Specific surface area 2 $m^2/g$) | 5.0 |
| Perfume | q.s. |
| Total: | 100.0 wt % |

Total surface area contained 1g of the composition: 10.1 $m^2$
Evaluation: Spreadability ⊚, Luster o, Secondary adhesion ⊚, Stickiness ⊚

Example 1-2 Paste-like rouge

| | |
|---|---|
| Vaseline | 10.0 wt % |
| Squalane | 15.0 |
| Castor oil | 3.0 |
| Glyceryl triisostearate | 2.0 |
| Silicone resin which has a molecular weight of about 5,000 and is expressed by mean formula of $(CH_3)_{1.33}SiO_{1.34}$ with $(CH_3)_3SiO_{1/2}:SiO_2$ unit = 0.8:1 | 25.0 |
| Decamethylcyclopentasiloxane | 39.5 |
| Silica (Specific surface area 200 $m^2/g$) | 2.5 |
| Pigment (Specific surface area 2 $m^2/g$) | 3.0 |
| Perfume | q.s. |
| Total: | 100.0 wt % |

Total surface area contained 1g of the composition: 5.06 $m^2$
Evaluation: Spreadability ⊚, Luster o, Secondary adhesion ⊚, Stickiness ⊚

Example 1-3 Emulsification-type lipstick

| | |
|---|---|
| Paraffin wax | 10.0 wt % |
| Microcrystalline wax | 4.0 |
| Glyceryl diisostearate | 7.0 |
| Macademia nut oil | 3.0 |
| Polybutene | 3.0 |
| Diisostearyl malate | 4.0 |
| Silicone resin which has a molecular weight of about 8,000 and is expressed by mean formula of $(CH_3)_{1.33}SiO_{1.34}$ with $(CH_3)_3SiO_{1/2}:SiO_2$ unit = 0.8:1 | 25.0 |
| Decamethylclopentasiloxane | 10.5 |
| Octamethylcyclotetrasiloxane | 5.0 |
| Dimethylpolysiloxane (Viscosity 6 cs) | 5.0 |
| Silica (Specific surface area 20 $m^2/g$) | 10.0 |
| Polyglyceryl diisostearate | 1.0 |
| Polyoxyethylene methylpolysiloxane copolymer | 2.0 |
| Ion-exchanged water | 5.0 |
| Glycerine | 1.0 |
| Pigment (Specific surface area 2 $m^2/g$) | 4.5 |
| Perfume | q.s. |
| Total: | 100.0 wt % |

Total surface area contained 1g of the composition: 2.09 $m^2$
Evaluation: Spreadability ⊚, Luster o, Secondary adhesion ⊚, Stickiness ⊚

Example 1-4 Lipstick

| | |
|---|---|
| Polyethylene wax | 8.0 wt % |
| Candelilla wax | 3.0 |
| Squalane | 8.0 |
| Macademia nut oil fatty acid ester | 2.5 |
| Glyceryl tri-2-ethyl hexanoate | 4.5 |
| Silicone resin which has a molecular weight of | 20.0 |

-continued about 6,000 and is expressed by mean formula of
$(CH_3)_{1.33}SiO_{1.34}$ with $(CH_3)_3SiO_{1/2}:SiO_2$ unit = 0.8:1

| | |
|---|---|
| Decamethylcyclopentasiloxane | 42.0 |
| Barium sulfate (Specific surface area 18.9 m²/g) | 5.0 |
| Silica (Specific surface area 200 m²/g) | 2.0 |
| Pigment (Specific surface area 2 m²/g) | 5.0 |
| Perfume | q.s. |
| Total: | 100.0 wt % |

Total surface area contained 1g of the composition: 5.045 m²

Evaluation: Spreadability ⊚, Luster o, Secondary adhesion ⊙, Stickiness ⊚

2. Example Of Compounding Of Silica

Example 2-1 Lipstick

| | |
|---|---|
| Glyceryl tri-2-ethyl hexanoate | 10.0 wt % |
| Ceresin wax | 8.0 |
| Carnauba wax | 2.0 |
| Mica | 10.0 |
| Silica | 5.0 |
| Dimethylpolysiloxane methyl (polyoxyethylene) copolymer | 2.0 |
| Octamethylcyclotetrasiloxane | 38.0 |
| Silicone resin which has a molecular weight of about 3,000 and is expressed by mean formula of $(CH_3)_{1.33}SiO_{1.34}$ with $(CH_3)_3SiO_{1/2}:SiO_2$ unit = 0.8:1 | 20.0 |
| Pigment | 5.0 |
| Antioxidant | q.s. |
| UV-absorber | q.s. |
| Perfume | q.s. |
| Total: | 100.0 wt % |

Evaluation: Spreadability ⊚, Luster o, Secondary adhesion ⊙, Stickiness ⊚

Example 2-2 Lipstick

| | |
|---|---|
| Glyceryl tri-2-ethyl hexanoate | 5.0 wt % |
| Dimethylpolysiloxane (Viscosity 20 cs) | 5.0 |
| Ceresin wax | 5.0 |
| Carnauba wax | 3.0 |
| Polyethylene wax | 3.0 |
| Mica | 18.0 |
| Silica | 2.0 |
| Decamethylcyclopentasiloxane | 36.0 |
| Silicone resin which has a molecular weight of about 5,000 and is expressed by mean formula of $(CH_3)_{1.0}SiO_{1.5}$ with $(CH_3)_3SiO_{1/2}:SiO_2$ unit = 0.5:1 | 15.0 |
| Pigment | 5.0 |
| Pearl agent | 3.0 |
| Antioxidant | q.s. |
| UV-absorber | q.s. |
| Perfume | q.s. |
| Total: | 100.0 wt% |

Evaluation: Spreadability ⊚, Luster o, Secondary adhesion ⊙, Stickiness ⊚

Example 2-3 Lipstick

| | |
|---|---|
| Liquid paraffin | 5.0 wt % |
| Dimethylpolysiloxane (Viscosity 20 cs) | 5.0 |
| Carnauba wax | 2.0 |
| Polyethylene wax | 8.0 |
| Mica | 7.0 |
| Silica | 8.0 |
| Dimethylpolysiloxane methyl (polyoxyethylene) copolymer | 1.0 |
| Octamethylcyclotetrasiloxane | 38.0 |
| Silicone resin which has a molecular weight of about 3,000 and is expressed by mean formula of $(CH_3)_{1.33}SiO_{1.34}$ with $(CH_3)_3SiO_{1/2}:SiO_2$ unit = 0.8:1 | 18.0 |
| Pigment | 3.0 |
| Pearl agent | 5.0 |
| Antioxidant | q.s. |
| UV-absorber | q.s. |
| Perfume | q.s. |
| Total: | 100.0 wt % |

Evaluation: Spreadability ⊚, Luster o, Secondary adhesion ⊙, Stickiness ⊚

Example 2-4 Lipstick

| | |
|---|---|
| Glyceryl tri-2-ethyl hexanoate | 5.0 wt % |
| Dimethylpolysiloxane (Viscosity 20 cs) | 5.0 |
| Castor oil | 3.0 |
| Ceresin wax | 4.0 |
| Carnauba wax | 4.0 |
| Polyethylene wax | 4.0 |
| Mica | 10.0 |
| Silica | 2.0 |
| Dimethylpolysiloxane methyl (polyoxyethylene) copolymer | 1.0 |
| Octamethylcyclotetrasiloxane | 20.0 |
| Decamethylcyclopentasiloxane | 19.0 |
| Silicone resin which has a molecular weight of about 5,000 and is expressed by mean formula of $(CH_3)_{1.0}SiO_{1.5}$ with $(CH_3)_3SiO_{1/2}:SiO_2$ unit = 0.5:1 | 30.0 |
| Pigment | 5.0 |
| Pearl agent | 3.0 |
| Antioxidant | q.s. |
| UV-absorber | q.s. |
| Perfume | q.s. |
| Total: | 100.0 wt % |

Evaluation: Spreadability ⊚, Luster o, Secondary adhesion ⊙, Stickiness ⊚

3. Example Of Compounding Of Titanated Mica

Example 3-1 Lipstick

| | |
|---|---|
| Ceresin wax | 15.0 wt % |
| Carnauba wax | 2.0 |
| Glyceryl diisostearate | 15.0 |
| Lanolin | 0.2 |
| Macademia nut oil | 0.1 |
| Diisostearyl malate | 3.0 |
| Trimethylolpropane tri-2-ethyl hexanoate | 1.5 |
| Glyceryl triisostearate | 1.5 |
| Silicone resin which has a molecular weight of about 3,000 and is expressed by mean formula of $(CH_3)_{1.33}SiO_{1.34}$ with $(CH_3)_3SiO_{1/2}:SiO_2$ unit = 0.8:1 | 30.0 |
| Octamethylcyclotetrasiloxane | 23.6 |
| Red #104-1 | 1.6 |
| Titanium dioxide | 1.5 |
| Titanated mica (Mica:TiO₂ = 55:45) | 5.0 |
| Perfume | q.s. |
| Total: | 100.0 wt % |

Evaluation: Spreadability ⊚, Luster o, Secondary adhesion ⊙, Stickiness ⊚

Example 3-2 Paste-like rouge

| | |
|---|---|
| Vaseline | 10.0 wt % |
| Squalane | 15.0 |
| Castor oil | 3.0 |
| Glyceryl triisostearate | 2.0 |
| Silicone resin which has a molecular weight of about 5,000 and is expressed by mean formula of $(CH_3)_{1.33}SiO_{1.34}$ with $(CH_3)_3SiO_{1/2}:SiO_2$ unit = 0.8:1 | 25.0 |
| Decamethylcyclopentasiloxane | 37.4 |
| Red #201 | 0.8 |
| Red iron oxide | 0.8 |
| Carmine coated Titanated mica (Mica:TiO₂:Carmine = 60:37:3) | 6.0 |
| Perfume | q.s. |
| Total: | 100.0 wt % |

Evaluation: Spreadability ⊚, Luster ⊚, Secondary adhesion ⊙, Stickiness ⊚

Example 3-3 Emulsification-type lipstick

| | |
|---|---|
| Paraffin wax | 10.0 wt % |
| Microcrystalline wax | 4.0 |

41

-continued

| | |
|---|---|
| Glyceryl diisostearate | 7.0 |
| Macademia nut oil | 3.0 |
| Polybutene | 3.0 |
| Diisostearyl malate | 4.0 |
| Silicone resin which has a molecular weight of about 8,000 and is expressed by mean formula of $(CH_3)_{1.33}SiO_{1.34}$ with $(CH_3)_3SiO_{1/2}:SiO_2$ unit = 0.8:1 | 30.0 |
| Decamethylcyclopentasiloxane | 12.2 |
| Octamethylcyclotetrasiloxane | 7.0 |
| Dimethylpolysiloxane (Viscosity 6 cs) | 5.0 |
| Silica | 0.5 |
| Synthetic sodium magnesium silicate | 1.0 |
| Polyoxyethylene methylpolysiloxane copolymer | 2.0 |
| Ion-exchanged water | 5.0 |
| Glycerine | 1.0 |
| Red #202 | 2.0 |
| Titanium dioxide | 0.3 |
| Red iron oxide coated titanated mica (Mica:$TiO_2$:Red iron oxide = 55:20:25) | 2.0 |
| Titanated mica (Mica:$TiO_2$ = 65:35) | 1.0 |
| Perfume | q.s. |
| Total: | 100.0 wt % |

Evaluation: Spreadability ⊚, Luster o, Secondary adhesion ⊚, Stickiness o

4. Example Of Combination Of Ultrafine Particle And Large-Size Particle

Example 4-1 Lipstick

| | |
|---|---|
| Ceresin wax | 15.0 wt % |
| Carnauba wax | 2.0 |
| Glyceryl diisostearate | 15.0 |
| Lanoline | 0.2 |
| Macademia nut oil | 0.1 |
| Diisostearyl malate | 3.0 |
| Trimethylolpropane tri-2-ethyl hexanoate | 1.5 |
| Glyceryl triisostearate | 1.5 |
| Silicone resin which has a molecular weight of about 3,000 and is expressed by mean formula of $(CH_3)_{1.33}SiO_{1.34}$ with $(CH_3)_3SiO_{1/2}:SiO_2$ unit = 0.8:1 | 30.0 |
| Octamethylcyclotetrasiloxane | 21.7 |
| Silica (Particle size 0.02 μm) | 5.0 |
| Red #202 (Particle size 0.933 μm) | 5.0 |
| Perfume | q.s. |
| Total: | 100.0 wt % |

Particle size ratio (Ultrafine particle/Large-size particle): 0.021
Evaluation: Spreadability ⊚, Luster o, Secondary adhesion ⊚, Stickiness ⊚

Example 4-2 Lipstick

| | |
|---|---|
| Ceresin wax | 15.0 wt % |
| Carnauba wax | 2.0 |
| Glyceryl diisostearate | 15.0 |
| Lanoline | 0.2 |
| Macademia nut oil | 0.1 |
| Diisostearyl malate | 3.0 |
| Trimethylolpropane tri-2-ethyl hexanoate | 1.5 |
| Glyceryl triisostearate | 1.5 |
| Silicone resin which has a molecular weight of about 3,000 and is expressed by mean formula of $(CH_3)_{1.33}SiO_{1.34}$ with $(CH_3)_3SiO_{1/2}:SiO_2$ unit = 0.8:1 | 30.0 |
| Octamethylcyclotetrasiloxane | 21.7 |
| Silica (Particle size 0.03 μm) | 5.0 |
| Titanated mica (Particle size 6.9 μm) | 5.0 |
| Perfume | q.s. |
| Total: | 100.0 wt % |

Particle size ratio (Ultrafine particle/Large-size particle): 0.0043
Evaluation: Spreadability ⊚, Luster o, Secondary adhesion ⊚, Stickiness ⊚

Example 4-3 Lipstick

| | |
|---|---|
| Ceresin wax | 15.0 wt % |
| Carnauba wax | 2.0 |

42

-continued

| | |
|---|---|
| Glyceryl diisostearate | 15.0 |
| Lanoline | 0.2 |
| Macademia nut oil | 0.1 |
| Diisostearyl malate | 3.0 |
| Trimethylolpropane tri-2-ethyl hexanoate | 1.5 |
| Glyceryl triisostearate | 1.5 |
| Silicone resin which has a molecular weight of about 3,000 and is expressed by mean formula of $(CH_3)_{1.33}SiO_{1.34}$ with $(CH_3)_3SiO_{1/2}:SiO_2$ unit = 0.8:1 | 30.0 |
| Octamethylcyclotetrasiloxane | 21.7 |
| Ultrafine barium sulfate (Particle size 0.08 μm) | 5.0 |
| Titanated mica (Particle size 6.9 μm) | 5.0 |
| Perfume | q.s. |
| Total: | 100.0 wt % |

Particle size ratio (Ultrafine particle/Large-size particle): 0.012
Evaluation: Spreadability ⊚, Luster o, Secondary adhesion ⊚, Stickiness ⊚

Example 4-4 Lipstick

| | |
|---|---|
| Polyethylene wax | 8.0 wt % |
| Candelilla wax | 3.0 |
| Squalane | 8.0 |
| Macademia nut oil fatty acid ester | 2.5 |
| Glyceryl tri-2-ethyl hexanoate | 4.5 |
| Silicone resin which has a molecular weight of about 6,000 and is expressed by mean formula of $(CH_3)_{1.33}SiO_{1.34}$ with $(CH_3)_3SiO_{1/2}:SiO_2$ unit = 0.8:1 | 20.0 |
| Decamethylcyclopentasiloxane | 44.0 |
| Silica (Particle size 0.02 μm) | 5.0 |
| Red #226 (Particle size 0.407 μm) | 5.0 |
| Perfume | q.s. |
| Total: | 100.0 wt % |

Particle size ratio (Ultrafine particle/Large-size particle): 0.049
Evaluation: Spreadability ⊚, Luster o, Secondary adhesion ⊚, Stickiness ⊚

Example 4-5 Emulsification-type lipstick

| | |
|---|---|
| Paraffin wax | 10.0 wt % |
| Microcrystalline wax | 4.0 |
| Glyceryl diisostearate | 7.0 |
| Macademia nut oil | 3.0 |
| Polybutene | 3.0 |
| Diisostearyl malate | 4.0 |
| Silicone resin which has a molecular weight of about 8,000 and is expressed by mean formula of $(CH_3)_{1.33}SiO_{1.34}$ with $(CH_3)_3SiO_{1/2}:SiO_2$ unit = 0.8:1 | 30.0 |
| Decamethylcyclopentasiloxane | 10.5 |
| Octamethylcyclotetrasiloxane | 7.0 |
| Dimethylpolysiloxane (Viscosity 6 cs) | 5.0 |
| Silica (Particle size 0.02 μm) | 3.0 |
| Synthetic sodium magnesium silicate | 1.0 |
| Polyoxyethylene methylpolysiloxane copolymer | 1.0 |
| Ion-exchanged water | 5.0 |
| Glycerine | 1.0 |
| Red iron oxide (Particle size 0.602 μm) | 4.5 |
| Perfume | q.s. |
| Total: | 100.0 wt % |

Particle size ratio (Ultrafine particle/Large-size particle): 0.033
Evaluation: Spreadability ⊚, Luster o, Secondary adhesion ⊚, Stickiness ⊚

Example 4-6 Paste-like rouge

| | |
|---|---|
| Vaseline | 10.0 wt % |
| Squalane | 15.0 |
| Castor oil | 3.0 |
| Glyceryl diisostearate | 2.0 |
| Silicone resin which has a molecular weight of about 5,000 and is expressed by mean formula of $(CH_3)_{1.33}SiO_{1.34}$ with $(CH_3)_3SiO_{1/2}:SiO_2$ unit = 0.8:1 | 25.0 |
| Decamethylcyclopentasiloxane | 39.5 |
| Silica (Particle size 0.02 μm) | 2.5 |
| Red #202 (particle size 0.933 μm) | 3.0 |
| Perfume | q.s. |
| Total: | 100.0 wt % |

Particle size ratio (Ultrafine particle/Large-size particle): 0.021

Evaluation: Spreadability ⊚, Luster o, Secondary adhesion ⊚, Stickiness ⊚

5. Example Of Turbidity Of Water-Repellent Polymer And Nonvolatile Oil Content

Example 5-1 Lipstick

| | |
|---|---|
| Ceresin wax | 15.0 wt % |
| Carnauba wax | 2.0 |
| Glyceryl diisostearate | 15.0 |
| Lanoline | 0.2 |
| Macadamia nut oil | 0.1 |
| Diisostearyl malate | 3.0 |
| Trimethylolpropane tri-2-ethyl hexanoate | 1.5 |
| Glyceryl triisostearate | 1.5 |
| Silicone resin which has a molecular weight of about 3,000 and is expressed by mean formula of $(CH_3)_{1.33}SiO_{1.34}$ with $(CH_3)_3SiO_{1/2}:SiO_2$ unit = 0.8:1 | 30.0 |
| Octamethylcyclotetrasiloxane | 21.7 |
| Silica | 5.0 |
| Pigment | 5.0 |
| Perfume | q.s. |
| Total: | 100.0 wt % |

Turbidity: 18.0
Evaluation: Spreadability ⊚, Luster o, Secondary adhesion ⊚, Stickiness ⊚

Example 5-2 Paste-like rouge

| | |
|---|---|
| Vaseline | 10.0 wt % |
| Squalane | 15.0 |
| Castor oil | 3.0 |
| Glyceryl triisostearate | 2.0 |
| Silicone resin which has a molecular weight of about 5,000 and is expressed by mean formula of $(CH_3)_{1.33}SiO_{1.34}$ with $(CH_3)_3SiO_{1/2}:SiO_2$ unit = 0.8:1 | 25.0 |
| Decamethylcyclopentasiloxane | 39.5 |
| Silica | 2.5 |
| Pigment | 3.0 |
| Perfume | q.s. |
| Total: | 100.0 wt % |

Turbidity: 20.5
Evaluation: Spreadability ⊚, Luster o, Secondary adhesion ⊚, Stickiness o

Example 5-3 Lipstick

| | |
|---|---|
| Polyethylene wax | 8.0 wt % |
| Candelilla wax | 3.0 |
| Squalane | 8.0 |
| Macadamia nut oil fatty acid ester | 2.5 |
| Glyceryl tri-2-ethyl hexanoate | 4.5 |
| Silicone resin which has a molecular weight of about 6,000 and is expressed by mean formula of $(CH_3)_{1.33}SiO_{1.34}$ with $(CH_3)_3SiO_{1/2}:SiO_2$ unit = 0.8:1 | 20.0 |
| Decamethylcyclopentasiloxane | 44.0 |
| Ultrafine barium sulfate | 5.0 |
| Pigment | 5.0 |
| Perfume | q.s. |
| Total: | 100.0 wt % |

Turbidity: 14.1
Evaluation: Spreadability ⊚, Luster o, Secondary adhesion ⊚, Stickiness ⊚

Example 5-4 Emulsification-type lipstick

| | |
|---|---|
| Paraffin wax | 10.0 wt % |
| Microcrystalline wax | 4.0 |
| Glyceryl diisostearate | 7.0 |
| Macadamia nut oil | 3.0 |
| Polybutene | 3.0 |
| Diisostearyl malate | 4.0 |
| Silicone resin which has a molecular weight of about 8,000 and is expressed by mean formula of $(CH_3)_{1.33}SiO_{1.34}$ with $(CH_3)_3SiO_{1/2}:SiO_2$ unit = 0.8:1 | 30.0 |
| Decamethylcyclopentasiloxane | 10.5 |
| Octamethylcyclotetrasiloxane | 7.0 |
| Dimethylpolysiloxane (Viscosity 6 cs) | 5.0 |
| Silica | 3.0 |
| Synthetic sodium magnesium silicate | 1.0 |
| Polyoxyethylene methylpolysiloxane copolymer | 2.0 |
| Ion-exchanged water | 5.0 |
| Glycerine | 1.0 |
| Pigment | 4.5 |
| Perfume | q.s. |
| Total: | 100.0 wt % |

Turbidity: 21.5
Evaluation: Spreadability ⊚, Luster o, Secondary adhesion ⊚, Stickiness ⊚

6. Example Of Combination Of Water-Repellent Polymer And Wax

Example 6-1 Lipstick

| | |
|---|---|
| Ceresin wax | 15.0 wt % |
| Carnauba wax | 2.0 |
| Glyceryl diisostearate | 15.0 |
| Lanoline | 0.2 |
| Macadamia nut oil | 0.1 |
| Diisostearyl malate | 3.0 |
| Trimethylolpropane tri-2-ethyl hexanoate | 1.5 |
| Glyceryl triisostearate | 1.5 |
| Silicone resin which has a molecular weight of about 3,000 and is expressed by mean formula of $(CH_3)_{1.33}SiO_{1.34}$ with $(CH_3)_3SiO_{1/2}:SiO_2$ unit = 0.8:1 | 30.0 |
| Octamethylcyclotetrasiloxane | 21.7 |
| Silica | 5.0 |
| Pigment | 5.0 |
| Perfume | q.s. |
| Total: | 100.0 wt % |

Evaluation: Spreadability ⊚, Luster o, Secondary adhesion ⊚, Stickiness ⊚
Powdery feel ⊚

Example 6-2 Lipstick

| | |
|---|---|
| Polyethylene wax | 8.0 wt % |
| Candelilla wax | 3.0 |
| Squalane | 8.0 |
| Macadamia nut oil fatty acid ester | 2.5 |
| Glyceryl tri-2-ethyl hexanoate | 4.5 |
| Silicone resin which has a molecular weight of about 6,000 and is expressed by mean formula of $(CH_3)_{1.33}SiO_{1.34}$ with $(CH_3)_3SiO_{1/2}:SiO_2$ unit = 0.8:1 | 20.0 |
| Decamethylcyclopentasiloxane | 44.0 |
| Silica | 5.0 |
| Pigment | 5.0 |
| Perfume | q.s. |
| Total: | 100.0 wt % |

Evaluation: Spreadability ⊚, Luster o, Secondary adhesion ⊚, Stickiness ⊚
Powdery feel ⊚

Example 6-3 Emulsification lipstick

| | |
|---|---|
| Paraffin wax | 10.0 wt % |
| Microcrystalline wax | 4.0 |
| Glyceryl diisostearate | 7.0 |
| Macadamia nut oil | 3.0 |
| Polybutene | 3.0 |
| Diisostearyl malate | 4.0 |
| Silicone resin which has a molecular weight of about 8,000 and is expressed by mean formula of $(CH_3)_{1.33}SiO_{1.34}$ with $(CH_3)_3SiO_{1/2}:SiO_2$ unit = 0.8:1 | 30.0 |
| Decamethylcyclopentasiloxane | 10.5 |
| Octamethylcyclotetrasiloxane | 7.0 |
| Dimethylpolysiloxane (Viscosity 6 cs) | 5.0 |
| Silica | 3.0 |
| Synthetic sodium magnesium silicate | 1.0 |
| Polyoxyethylene methylpolysiloxane copolymer | 2.0 |
| Ion-exchanged water | 5.0 |
| Glycerine | 1.0 |

| | |
|---|---|
| Pigment | 5.0 |
| Perfume | q.s. |
| Total: | 100.0 wt % |

Evaluation: Spreadability ⊚, Luster o, Secondary adhesion ⊚, Stickiness ⊚
Powdery feel ⊚

Example 6-4 Lipstick

| | |
|---|---|
| Ceresin wax | 15.0 wt % |
| Carnauba wax | 2.0 |
| Glyceryl diisostearate | 15.0 |
| Lanoline | 0.2 |
| Macademia nut oil | 0.1 |
| Diisostearyl malate | 3.0 |
| Trimethylolpropane tri-2-ethyl hexanoate | 1.5 |
| Glyceryl triisostearate | 1.5 |
| Silicone resin which has a molecular weight of about 3,000 and is expressed by mean formula of $(CH_3)_{1.33}SiO_{1.34}$ with $(CH_3)_3SiO_{1/2}:SiO_2$ unit = 0.8:1 | 30.0 |
| Octamethylcyclotetrasiloxane | 21.7 |
| Silica | 5.0 |
| Titanated mica | 3.0 |
| Pigment | 2.0 |
| Perfume | q.s. |
| Total: | 100.0 wt % |

Evaluation: Spreadability ⊚, Luster o, Secondary adhesion ⊚, Stickiness o
Powdery feel o

7. Example Of Compounding Of Water

Example 7-1 Lipstick

| | |
|---|---|
| Glyceryl tri-2-ethyl hexanoate | 10.0 wt % |
| Ceresin wax | 8.0 |
| Carnauba wax | 2.0 |
| Mica | 10.0 |
| Silica | 5.0 |
| Octamethylcyclotetrasiloxane | 36.0 |
| Polyatel-denatured dimethylpolysiloxane (Viscosity 220 cs) | 0.5 |
| Veegum HV (R. T. Vanderbuilt) | 3.0 |
| Purified water | 0.5 |
| Silicone resin which has a molecular weight of about 5,000 and is expressed by mean formula of $(CH_3)_{1.0}SiO_{1.5}$ with $(CH_3)_3SiO_{1/2}:SiO_2$ unit = 0.5:1 | 20.0 |
| Pigment | 5.0 |
| Antioxidant | q.s. |
| UV-absorber | q.s. |
| Perfume | q.s. |
| Total: | 100.0 wt % |

Evaluation: Luster o, Secondary adhesion ⊚, Wetness ⊚

Example 7-2 Lipstick

| | |
|---|---|
| Glyceryl tri-2-ethyl hexanoate | 5.0 wt % |
| Dimethylpolysiloxane (Viscosity 20 cs) | 4.5 |
| Ceresin wax | 5.0 |
| Carnauba wax | 3.0 |
| Polyethylene wax | 3.0 |
| Mica | 12.0 |
| Silica | 2.0 |
| Decamethylcyclopentasiloxane | 36.0 |
| Silicone resin which has a molecular weight of about 5,000 and is expressed by mean formula of $(CH_3)_{1.0}SiO_{1.5}$ with $(CH_3)_3SiO_{1/2}:SiO_2$ unit = 0.5:1 | 15.0 |
| Montmorillonite (Kunipia G-4; Kuniminekouka K K) | 4.0 |
| Natural water (Source area: Mount Tanigawadake) | 2.0 |
| Glycerine | 0.5 |
| Pigment | 5.0 |
| Pearl agent | 3.0 |
| Antioxidant | q.s. |
| UV-absorber | q.s. |
| Perfume | q.s. |
| Total: | 100.0 wt % |

Evaluation: Luster o, Secondary adhesion ⊚, Wetness o

Example 7-3 Lipstick

| | |
|---|---|
| Liquid paraffin | 5.0 wt % |
| Dimethylpolysiloxane (Viscosity 20 cs) | 5.0 |
| Carnauba wax | 2.0 |
| Polyethylene wax | 8.0 |
| Mica | 7.0 |
| Silica | 8.0 |
| Dimethylpolysiloxane methyl (polyoxyethylene) copolymer | 1.0 |
| Octamethylcyclotetrasiloxane | 34.9 |
| Silicone resin which has a molecular weight of about 3,000 and is expressed by mean formula of $(CH_3)_{1.33}SiO_{1.34}$ with $(CH_3)_3SiO_{1/2}:SiO_2$ unit = 0.8:1 | 18.0 |
| Glycerol monoorate | 3.0 |
| Natural water (Source area: Japan South Alps) | 0.1 |
| Pigment | 3.0 |
| Pearl agent | 5.0 |
| Antioxidant | q.s. |
| UV-absorber | q.s. |
| Perfume | q.s. |
| Total: | 100.0 wt % |

Evaluation: Luster o, Secondary adhesion ⊚, Wetness o

Example 7-4 Lipstick

| | |
|---|---|
| Glyceryl tri-2-ethyl hexanoate | 5.0 wt % |
| Dimethylpolysiloxane (Viscosity 20 cs) | 3.0 |
| Castor oil | 3.0 |
| Ceresin wax | 4.0 |
| Carnauba wax | 4.0 |
| Polyethylene wax | 4.0 |
| Mica | 10.0 |
| Silica | 2.0 |
| Dimethylpolysiloxane methyl(polyoxyethylene) copolymer | 1.0 |
| Octamethylcyclotetrasiloxane | 17.9 |
| Decamethylcyclopentasiloxane | 19.0 |
| Silicone resin which has a molecular weight of about 3,000 and is expressed by mean formula of $(CH_3)_{1.33}SiO_{1.34}$ with $(CH_3)_3SiO_{1/2}:SiO_2$ unit = 0.8:1 | 15.0 |
| Polyatel-denatured dimethylpolysiloxane (Viscosity 220 cs) | 1.0 |
| Synthetic hectorite (Laponite XLG; Laporte PLC in the United Kingdom) | 3.0 |
| Water | 0.1 |
| Pigment | 5.0 |
| Pearl agent | 3.0 |
| Antioxidant | q.s. |
| UV-absorber | q.s. |
| Perfume | q.s. |
| Total: | 100.0 wt % |

Evaluation: Luster ⊚, Secondary adhesion o, Wetness ⊚

We claim:

1. A composition for rouge for lip comprising:

a volatile oil content, a water-repellent polymer soluble to said volatile oil content, a powder wherein said powder has a total surface area of 1 to 25 m² per gram of the composition, and a nonvolatile oil content having a compatibility with said volatile oil content.

2. A composition for rouge for lip according to claim 1, wherein said composition contains:

10 to 60% by weight of the volatile oil content, 5 to 35% by weight of the water-repellent polymer, 1 to 25% by weight of the powder, and 5 to 40% by weight of the nonvolatile oil content.

3. A composition for rouge for lip according to claim 1, wherein said composition contains:

10 to 50% by weight of the volatile oil content, 10 to 35% by weight of the water-repellent polymer, 1 to 25% by weight of the powder, and 10 to 40% by weight of the nonvolatile oil content.

4. A composition for rouge for lip according to claim 1, wherein the powder is capable of being coated with the water-repellent polymer in a state where the volatile oil content does not exist therein.

5. A composition for rouge for lip according to claim 4, wherein at least a part of the powder is silica.

6. A composition for rouge for lip according to claim 4, wherein said composition contains:

20 to 60% by weight of the volatile oil content, 5 to 20% by weight of the water-repellent polymer, 1 to 10% by weight of silica, and 5 to 30% by weight of the nonvolatile oil content.

7. A composition for rouge for lip according to claim 1, wherein at least a part of the powder is titanated mica.

8. A composition for rouge for lip according to claim 1, wherein said composition contains:

10 to 50% by weight of the volatile oil content, 10 to 35% by weight of the water-repellent polymer, 1 to 10% by weight of titanated mica, and 10 to 40% by weight of the nonvolatile oil content.

9. A composition for rouge for lip according to claim 7, wherein said composition has a amount ratio of titanated mica/water-repellent polymer of 1/30 to 1/3.

10. A composition for rouge for lip according to claim 7, wherein said composition has a amount ratio of titanated mica/water-repellent polymer of 1/10 to 1/4.

11. A composition for rouge for lip according to claim 1, wherein at least a large-size particle and an ultrafine particle exist as the powder, wherein the ultrafine particle has a particle size of 0.01 to 0.1 μm, and wherein the ratio of the particle size of the ultrafine particle to the particle size of the large-size particle is 1:20 to 1:500.

12. A composition for rouge for lip according to claim 11, wherein said composition contains:

10 to 50% by weight of the volatile oil content, 10 to 35% by weight of the water-repellent polymer, 2 to 20% by weight of the powder, and 10 to 40% by weight of the nonvolatile oil content.

13. A composition for rouge for lip according to claim 11, wherein the amount ratio of the ultrafine particle to the large-size particle is preferably 1:19 to 10:1.

14. A composition for rouge for lip according to any of claim 11, wherein the ultrafine particle is ultrafine silica.

15. A composition for rouge for lip comprising:

a volatile oil content, a water-repellent polymer soluble to said volatile oil content, a powder wherein said powder has a total surface area of 1 to 25 m² per gram of the composition, and a nonvolatile oil content having a compatibility with said volatile oil content, said water-repellent polymer and said nonvolatile oil content yield a turbidity of 9.0 to 25.5 when they are mixed alone.

16. A composition for rouge for lip according to claim 15, wherein said composition contains:

10 to 50% by weight of the volatile oil content, 10 to 35% by weight of the water-repellent polymer, 0.1 to 25% by weight of the powder, and 10 to 40% by weight of the nonvolatile oil content.

17. A composition for rouge for lip according to claim 15, wherein, as the nonvolatile oil content, an oil content having a plasticizing capacity with respect to the water-repellent polymer and an oil content having no plasticizing capacity with respect to the water-repellent polymer are used to adjust the turbidity.

18. A composition for rouge for lip according to any of claim 15, wherein at least a part of the powder is silica.

19. A composition for rouge for lip according to claim 18, wherein said composition contains 0.1 to 10% by weight of silica.

20. A composition for rouge for lip comprising:

a volatile oil content, a water-repellent polymer soluble to said volatile oil content, a powder wherein said powder has a total surface area of 1 to 25 m² per gram of the composition, wax dispersible in said volatile oil content, and a nonvolatile oil content having a compatibility with said volatile oil content, wherein the compounding ratio of said water-repellent polymer to said wax is 10/3 to 5/7.

21. A composition for rouge for lip according to claim 20, wherein said composition contains:

10 to 50% by weight of the volatile oil content, 10 to 35% by weight of the water-repellent polymer, 1 to 20% by weight of the powder, 5 to 25% by weight of the wax, and 10 to 40% by weight of the nonvolatile oil content.

22. A composition for rouge for lip according to claim 20, wherein at least a part of the powder is silica.

23. A composition for rouge for lip according to claim 22, wherein said composition contains 1 to 10% by weight of silica.

24. A composition for rouge for lip according to claim 1, further containing water.

25. A composition for rouge for lip according to claim 22, wherein said composition contains 0.05 to 5% by weight of water.

26. A composition for rouge for lip according to claim 22, wherein the water compounded therein is natural water.

27. A composition for rouge for lip according to claim 1, wherein the volatile oil content is a silicone oil, while the water-repellent polymer is a silicone resin.

28. A composition for rouge for lip according to claim 1, wherein the weight ratio of the water-repellent polymer to the nonvolatile oil content is 1/2 to 2/1.

29. A composition for rouge for lip according to claim 1, wherein said water-repellent polymer is a silicone resin.

30. A composition for rouge for lip according to claim 15, wherein said water-repellent polymer is a silicone resin.

31. A composition for rouge for lip according to claim 20, wherein said water-repellent polymer is a silicone resin.

* * * * *